US008742091B2

(12) United States Patent
Terada et al.

(10) Patent No.: US 8,742,091 B2
(45) Date of Patent: Jun. 3, 2014

(54) METHOD OF PROMOTING NUCLEIC ACID TRANSFER

(75) Inventors: Masaaki Terada, Tokyo-to (JP); Takahiro Ochiya, Tokyo-to (JP); Yu Aso, Tokyo-to (JP); Kimi Honma, Tokyo-to (JP); Akihiko Sano, Ibaraki (JP); Shunji Nagahara, Ibaraki (JP)

(73) Assignees: Dainippon Sumitomo Pharma Co., Ltd., Osaka-Shi (JP); Koken Co., Ltd., Tokyo (JP); National Cancer Center, Tokyo (JP)

( * ) Notice: Subject to any disclaimer, the term of this patent is extended or adjusted under 35 U.S.C. 154(b) by 963 days.

(21) Appl. No.: 10/481,511

(22) PCT Filed: Jun. 20, 2002

(86) PCT No.: PCT/JP02/06137

§ 371 (c)(1),
(2), (4) Date: Dec. 19, 2003

(87) PCT Pub. No.: WO03/000297

PCT Pub. Date: Jan. 3, 2003

(65) Prior Publication Data

US 2004/0266004 A1    Dec. 30, 2004

(30) Foreign Application Priority Data

Jun. 20, 2001 (JP) ................. 2001-186320
Sep. 13, 2001 (JP) ................. 2001-278293

(51) Int. Cl.
C07H 21/02 (2006.01)
A61K 38/17 (2006.01)
C12N 15/11 (2006.01)

(52) U.S. Cl.
USPC .................. 536/24.5; 530/356; 514/44 A

(58) Field of Classification Search
None
See application file for complete search history.

(56) References Cited

U.S. PATENT DOCUMENTS

| 3,943,238 | A | | 3/1976 | Kobayashi et al. | |
|---|---|---|---|---|---|
| 5,069,936 | A | * | 12/1991 | Yen | 427/213.33 |
| 5,078,997 | A | | 1/1992 | Hora et al. | |
| 5,098,890 | A | * | 3/1992 | Gewirtz et al. | 514/44 |
| 5,264,618 | A | * | 11/1993 | Felgner et al. | 560/224 |
| 5,542,935 | A | * | 8/1996 | Unger et al. | 604/190 |
| 5,563,255 | A | * | 10/1996 | Monia et al. | 536/24.31 |
| 5,583,034 | A | * | 12/1996 | Green et al. | 435/6 |
| 5,614,587 | A | | 3/1997 | Rhee et al. | |
| 5,646,042 | A | | 7/1997 | Stinchcomb et al. | |
| 5,672,301 | A | * | 9/1997 | Orly et al. | 264/4.1 |
| 5,679,782 | A | * | 10/1997 | Rosenberg et al. | 536/23.1 |
| 5,807,581 | A | | 9/1998 | Rosenblatt et al. | |
| 5,844,107 | A | | 12/1998 | Hanson et al. | |
| 5,874,006 | A | * | 2/1999 | Lee et al. | 210/651 |
| 5,936,035 | A | | 8/1999 | Rhee et al. | |
| 6,025,337 | A | * | 2/2000 | Truong et al. | 514/44 |
| 6,068,857 | A | * | 5/2000 | Weitschies et al. | 424/489 |
| 6,218,112 | B1 | * | 4/2001 | Thatcher et al. | 435/6 |
| 6,312,732 | B1 | * | 11/2001 | Sokoll et al. | 424/501 |
| 6,331,525 | B1 | * | 12/2001 | Chiou et al. | 514/44 R |
| 6,524,613 | B1 | * | 2/2003 | Steer et al. | 424/450 |
| 6,537,813 | B1 | * | 3/2003 | Chen et al. | 435/455 |
| 6,680,301 | B2 | | 1/2004 | Berg et al. | |
| 6,969,400 | B2 | | 11/2005 | Rhee et al. | |
| 6,998,268 | B2 | * | 2/2006 | Terada et al. | 435/455 |
| 7,033,829 | B2 | | 4/2006 | Gilchrest et al. | |
| 7,052,875 | B1 | | 5/2006 | Terada et al. | |
| 7,345,027 | B2 | | 3/2008 | Tolentino et al. | |
| 7,521,431 | B2 | | 4/2009 | Reich et al. | |
| 7,585,848 | B2 | | 9/2009 | Masuda et al. | |
| 7,812,002 | B2 | | 10/2010 | Feinstein | |
| 7,825,101 | B2 | | 11/2010 | Mehta et al. | |
| 7,842,674 | B2 | | 11/2010 | Feinstein et al. | |
| 7,858,593 | B2 | | 12/2010 | Carmeliet et al. | |
| 7,902,167 | B2 | | 3/2011 | Farnebo et al. | |
| 8,106,024 | B2 | * | 1/2012 | Ochiya et al. | 514/44 A |
| 8,129,354 | B2 | | 3/2012 | Dorn et al. | |
| 8,148,346 | B2 | | 4/2012 | Banchereau et al. | |
| 8,187,823 | B2 | | 5/2012 | Coull et al. | |
| 8,193,163 | B2 | | 6/2012 | Reich et al. | |
| 8,198,259 | B2 | | 6/2012 | Dorn et al. | |
| 8,227,434 | B1 | | 7/2012 | Dalton et al. | |
| 8,227,444 | B2 | | 7/2012 | Dejneka | |
| 8,232,256 | B2 | | 7/2012 | Kaufmann et al. | |
| 8,236,775 | B2 | | 8/2012 | Reich et al. | |

(Continued)

FOREIGN PATENT DOCUMENTS

| CN | 1193916 A | | 9/1998 |
|---|---|---|---|
| EP | 0 268 421 A2 | * | 5/1988 |
| EP | 0412554 A2 | | 2/1991 |
| EP | 870839 A1 | | 10/1995 |
| EP | 0747066 A2 | | 12/1996 |
| EP | 0779362 | | 6/1997 |
| EP | 0 844 004 A1 | * | 5/1998 |
| EP | 844004 A1 | | 5/1998 |
| EP | 0844004 A1 | | 5/1998 |
| EP | 1043021 A1 | | 12/1998 |

(Continued)

OTHER PUBLICATIONS

Cortesi et al (Int. J. Pharm. 105(2): 181-186, 1994).*
Honma et al (Biochem. Biophys. Res. Comm. 289: 1075-1081, 2001).*
Honma et al (Biochem. Biophys. Res. Comm. 289: 1075-1081 (2001).*

(Continued)

*Primary Examiner* — Richard Schnizer
(74) *Attorney, Agent, or Firm* — Roberts Mlotkowski Safran & Cole, P.C.

(57) ABSTRACT

Means for transferring efficiently a desired nucleic acid into a cell is provided.
The present invention comprises using a complex comprising a collagen or a collagen derivative, and a desired nucleic acid.

10 Claims, 19 Drawing Sheets

(56) References Cited

U.S. PATENT DOCUMENTS

| | | |
|---|---|---|
| 2002/0115219 A1 | 8/2002 | Kobayashi et al. |
| 2003/0082161 A1 | 5/2003 | Terada et al. |
| 2004/0052840 A1 | 3/2004 | Kubota et al. |
| 2004/0266004 A1 | 12/2004 | Terada et al. |
| 2006/0258602 A1 | 11/2006 | Ando et al. |

FOREIGN PATENT DOCUMENTS

| | | |
|---|---|---|
| EP | 1078639 A1 | 2/2001 |
| EP | 1295611 A1 | 3/2003 |
| EP | 1407787 A1 | 4/2004 |
| EP | 1550463 A1 | 7/2005 |
| JP | 64-016581 A | 1/1989 |
| JP | 01-157388 A | 6/1989 |
| JP | 03-093716 | 9/1989 |
| JP | 04-091783 | 3/1992 |
| JP | 09-071542 A | 3/1997 |
| JP | 09-099052 A | 4/1997 |
| JP | 11-127843 A | 5/1999 |
| JP | 2000-184502 * | 6/2000 |
| JP | 2001-252068 | 9/2001 |
| JP | 2001-252068 A | 9/2001 |
| JP | 2002-325572 | 11/2002 |
| JP | 2003-274950 A | 9/2003 |
| JP | 2001-335512 A | 12/2004 |
| WO | WO 95/22611 | 8/1995 |
| WO | WO 96/14424 A1 | 5/1996 |
| WO | WO 97/02047 | 1/1997 |
| WO | WO 97/15330 | 5/1997 |
| WO | WO-99/02135 A1 | 1/1999 |
| WO | WO 99/61063 * | 12/1999 |
| WO | WO 99/61063 A1 | 12/1999 |
| WO | WO 00/73414 A1 | 12/2000 |
| WO | WO 01/34206 * | 5/2001 |
| WO | WO 01/34206 A2 | 5/2001 |
| WO | WO 01/97857 A1 | 12/2001 |
| WO | WO 03/000297 A1 | 1/2003 |
| WO | WO 2004/002643 A1 | 1/2004 |

OTHER PUBLICATIONS

Takeshita et al (Proc. Nat. Acad. Sci 102(34): 12177-12182 (2005).*
Ishimoto et al (Mol. Ther. 16: 387-395, 2008).*
Kinouchi et al (Gene Therapy (2008) 1-6).*
Hanai et al (Human Gene Therapy 15: 263-272, 2004).*
Bennett et al (J. Pharm. Exp. Ther. 280(2): 988-1000, 1997).*
Dean et al (Cancer Res. 56: 3499-3507, 1996).*
Mui et al (J. Pharm. Exp. Ther. 298(3): 1185-1192, 2001).*
Putney et al (Antisense & Nucl. Acid Drug Dev. 9: 451-458, 1999).*
Rait et al (Mol. Med. 8(8): 475-486, 2002).*
Rijcken et al (Gut 51: 529-535, 2002).*
Saitoh et al (Exp. Lung Res. 28: 219-231, 2002).*
Sugano et al (J. Biol. Chem. 273(9): 5033-5036, 1998).*
Whitmore et al (Cancer Immunol. Immunother. 50: 503-514, 2001).*
Takei et al (Cancer Res. 61: 8486-8491, 2001).*
Lemieux et al (J. Drug Targ. 8(2): 91-105, 2000).*
Ochiya et al (Nature Med. 5(6): 707-710, 1999).*
Bonnet et al (Pharmaceutical Research, vol. 25, No. 12, Dec. 2008).*
Filleur et al (Cancer Research 63, 3919-3922, Jul. 15, 2003).*
Cover photo from Proc. Nat. Acad. Sci. USA 102(34), 2005.*
Cover information for Proc. Nat. Acad. Sci. USA 102(34), 2005.*
Inaba et al (Mol. Ther. 20(2): 356-366(2012)).*
Honma et al., Biochemical and Biophysical Research Communications, vol. 289, No. 5, pp. 1075-1081 (2001).
P.L. Foster et al., Proc. Natl. Acad. Sci. USA, vol. 84, May 1987, pp. 2891-2895.
J.J. Donnelly et al., Journal of Immunological Methods, vol. 176, 1994, pp. 145-152.
S. Gay et al., Journal of Immunology, vol. 135, No. 2, Aug. 1985, pp. 1097-1100.
H. Kitamura et al., International Journal of Biological Macromolecules, vol. 20, 1997, p. 241-244.
Takahiro Ochiya et al., Biomaterial for Gene Delivery, Atelocollagen-mediated Controlled Release of Molecular Medicines, Current Gene Therapy, May 2001, vol. 1, No. 1.
Ochiya et al., Nature Medicine, vol. 5, No. 6, Jun. 1999, pp. 707-710.
Friess, Collagen-Biomaterial for drug delivery, (1998) European Journal of Pharmaceutics and Biopharmaceutics. vol. 45, pp. 113-136.
Juliano, R. et al. "Aspects of the Transport and Delivery of Antisense Oligonucleotides," Current Opinion in Molecular Therapeutics, vol. 2, No. 3, pp. 297-303 (2000).
Ochiya, T. et al. "Antisense Approaches to in Vitro Organ Culture," Methods in Enzymology, vol. 314, pp. 401-411 (1999).
Supplemental European Search Report mailed Jun. 9, 2009 in EP 01938732.
Mah, Cathryn et al., Virus-Based Gene Delivery Systems, Clin Pharmacokinet, 2002, vol. 41, pp. 901-911.
Gehl, J., Electroporation: theory and methods, perspectives for drug delivery, gene therapy and research, Acta Physiol Scand, 2003, vol. 177, pp. 437-447.
Batard, Pascal et al., Transfer of high copy number plasmid into mammalian cells by calcium phosphate transfection, Gene, 2001, vol. 270, pp. 61-68.
Holter, Wolfgang et al., Efficient Gene Transfer by Sequential Treatment of Mammalian Cells with DEAE-Dextran and Deoxyribonucleic Acid, Experimental Cell Research, 1989, vol. 184, pp. 546-551.
Rocha, A. et al., Improvement of DNA transfection with cationic liposomes, J. Physiol. Biochem., 2002, vol. 58, pp. 45-56.
De Smedt, Stefaan C. et al., Cationic Polymer Based Gene Delivery Systems, Pharmaceutical Research, vol. 17, 2000, pp. 113-126.
Morrison, D.A., Transformation in *Escherichia coli*: Cryogenic Preservation of Competent Cells, Journal of Bacteriology, vol. 132, No. 1, pp. 349-351, Oct. 1977.
Mandel et al., Calcium-dependent Bacteriophage DNA Infection, J. Mol. Biol., vol. 53, No. 1, pp. 159-162, 1970.
Graham et al., Transformation of Rat Cells by DNA of Human Ad Virology, vol. 54, No. 2, pp. 536-539, 1973.
Takei et al., Cancer Res., vol. 61: 8486-8491, 2001.
Whitmore et al., Cancer Immunol. Immunother., vol. 50: 503-514, 2001.
Sugano et al., J. Biol. Chem., vol. 273(9): 5033-5036, 1998.
Saitoh et al., Exp. Lung Res., vol. 28: 219-231, 2002.
Rijcken et al., Gut, vol. 51: 529-535, 2002.
Rait et al., Mol. Med., vol. 8(8): 475-486, 2002.
Putney et al., Antisense & Nucl. Acid Drug Dev., vol. 9:451-458, 1999.
Mui et al., J. Pharm. Exp. Ther., vol. 298(3): 1185-1192, 2001.
Dean et al., Cancer Res., vol. 56:3499-3507, 1996.
Bennett et al., J. Pharm. Exp. Ther., vol. 280 (2):988-1000,1997.
Honma et al., Biochem. Biophys. Res. Comm., vol. 289: 1075-1081 (2001).
Takeshita et al., Proc. Natl. Acad. Sci, vol. 102(34): 12177-12182 (2005).
Ishimoto et al., Mol. Ther. vol. 16: 387-395 (2008).
Kinouchi et al., Gene Therapy, vol. 1-6 (2008).
Hanai et al., Human Gene Therapy, vol. 15: 263-272 (2004).
Foster et al., Proc. Natl. Acad. Sci. USA, vol. 84, May 1987, pp. 2891-2895.
Donnelly et al., Journal of Immunological Methods, vol. 176, 1994, pp. 145-152.
Gay et al., Journal of Immunology, vol. 135, No. 2, Aug. 1985, pp. 1097-1100.
Kitamura et al., International Journal of Biological Macromolecules, vol. 20, 1997, pp. 241-244.
Ochitani, Gene & Medicine, vol. 6, No. 1, pp. 21-25 (2002).
Cortesi et al., Int. Journal Pharm., vol. 105, No. 2, pp. 181-186 (1994).
Ochiya, T. "Controlled Gene Delivery Through Atelocollagen Implant," Experimental Medicine, 1999, vol. 17, No. 17, pp. 2288-2291.
Ochiya, T. et al., Biomaterial for Gene Delivery, Atelocollagen-mediated Controlled Release of Molecular Medicines, Current Gene Therapy, May 2001, vol. 1, No. 1.

(56) References Cited

OTHER PUBLICATIONS

Haberland et al., "Histone H1-mediated transfection: Serum inhibition can be overcome by Ca ions." Pharmaceutical Res. vol. 17, pp. 229-235, 2000.
Lam et al. "Calcium enhances the transfection potency of plasmid DNA-cationic liposome complexes," BBA, vol. 1463, pp. 279-290, 2000.
Haberland et al., "Calcium ions as efficient cofactor of polycation-mediated gene transfer." BBA, vol. 1445, pp. 21-30, 1999.
International Search Report for PCT/JP2002/06137; Oct. 1, 2002.
Supplemental European Search Report mailed Nov. 23, 2006 in EP 04807517.
Takei, Y. et al., The Journal of Bio. Chem., vol. 277, No. 26, pp. 23800-23806 (2002).
Takei, Y. et al., Cancer Research, vol. 64, pp. 3365-3370 (2004).
Sioud, M. et al., Biochemical and Biophysical Research Communications, vol. 312, pp. 1220-1225, (2003).
Nozawa, H. et al., Cancer Sci., vol. 97, No. 10, pp. 1115-1124 (2006).
Nakazawa, K. et al., Amer. Cancer Society, vol. 109, pp. 993-1002 (2007).
Kokuryo, T. et al., Cancer Res., vol. 67, No. 20, pp. 9637-9642 (2007).
Minakuchi, Y. et al, Nucleic Acids Research, vol. 32. No. 13, pp. 1-7 (2004).
Iwaki, K. et al., Int. J. Cancer, vol. 122, pp. 658-663 (2008).
Fuji, T. et al., Intl. J. Of Oncology, vol. 29, pp. 541-548 (2006).
Banno, H. et al., Society of Vascular Surgery, vol. 44, No. 3, pp. 633-641 (2006).
Office Action for U.S. Appl. No. 10/481,511 dated Nov. 25, 2009.
Office Action for U.S. Appl. No. 10/481,511 dated May 8, 2009.
Office Action for U.S. Appl. No. 10/481,511 dated Jan. 21, 2009.
Office Action for U.S. Appl. No. 10/481,511 dated Jun. 3, 2008.
Office Action for U.S. Appl. No. 10/481,511 dated Apr. 17, 2008.
Office Action for U.S. Appl. No. 10/481,511 dated Aug. 30, 2007.
Office Action for U.S. Appl. No. 10/481,511 dated Apr. 10, 2007.
Office Action for U.S. Appl. No. 10/481,511 dated Aug. 25, 2006.
Office Action for U.S. Appl. No. 10/311,621 dated Feb. 8, 2006.
Office Action for U.S. Appl. No. 10/311,621 dated Oct. 16, 2006.
Office Action for U.S. Appl. No. 10/311,621 dated Oct. 9, 2007.
Office Action for U.S. Appl. No. 10/311,621 dated Jul. 23, 2008.
Office Action for U.S. Appl. No. 10/311,621 dated Mar. 19, 2009.
Office Action for U.S. Appl. No. 10/311,621 dated Oct. 27, 2009.
Office Action for U.S. Appl. No. 12/486,703 dated Feb. 23, 2010.
Office Action for U.S. Appl. No. 10/583,277 dated Mar. 4, 2010.
Office Action for U.S. Appl. No. 10/583,277 dated Jun. 17, 2009.
Office Action for U.S. Appl. No. 11/909,457 dated Jan. 12, 2010.
Office Action for U.S. Appl. No. 11/909,457 dated Jun. 29, 2009.
Office Action for U.S. Appl. No. 10/481,511 dated May 12, 2006.
Office Action for U.S. Appl. No. 10/583,277 dated Mar. 13, 2009.
Lee, C. H., et al., "Biomedical applications of collagen," Int. J. Pharma., vol. 221, pp. 1-22 (2001).
Templeton et al., "Improved DNA: liposome complexes for increased systemic delivery and gene expression", Nature Biotechnology, vol. 15, Jul. 1997, pp. 647-652.
United States Office Action, dated Jun. 28, 2013, for U.S. Appl. No. 12/554,846.

* cited by examiner 1. 5 μg/ml pCAHST-1            ⎫  10mM Tris-HCl
2. 5 μg/ml pCAHST-1、100 μg/ml collagen  ⎭  0.15M NaCl
3. 5 μg/ml pCAHST-1            ⎫  10mM Tris-HCl
4. 5 μg/ml pCAHST-1、100 μg/ml collagen  ⎭  0.2M NaCl
5. 5 μg/ml pCAHST-1            ⎫  10mM Tris-HCl
6. 5 μg/ml pCAHST-1、100 μg/ml collagen  ⎭  1.0M NaCl
7.
8. Marker Photograph under a condition
of F3.5 for 1.5 sec

Fig. 3

Lane
Gel-980626-1
1. Marker
2. 5 μg/ml pCAHST-1
3. 5 μg/ml pCAHST-1+1.0 μg/ml Col.
4. 5 μg/ml pCAHST-1+10 μg/ml Col.
5. 5 μg/ml pCAHST-1+50 μg/ml Col.
6. 5 μg/ml pCAHST-1+100 μg/ml Col.
7. 5 μg/ml pCAHST-1+200 μg/ml Col.
8. 5 μg/ml pCAHST-1+300 μg/ml Col.

Gel-980626-2
1. 5 μg/ml pCAHST-1+1.0mg/ml heparan sulfate
2. 5 μg/ml pCAHST-1+1.0 μg/ml Col.+1.0mg/ml heparan sulfate
3. 5 μg/ml pCAHST-1+1.0 μg/ml Col.+1.0mg/ml heparan sulfate
4. 5 μg/ml pCAHST-1+1.0 μg/ml Col.+1.0mg/ml heparan sulfate
5. 5 μg/ml pCAHST-1+1.0 μg/ml Col.+1.0mg/ml heparan sulfate
6. 5 μg/ml pCAHST-1+1.0 μg/ml Col.+1.0mg/ml heparan sulfate
7. 5 μg/ml pCAHST-1+1.0 μg/ml Col.+1.0mg/ml heparan sulfate
8. Marker

[Results]

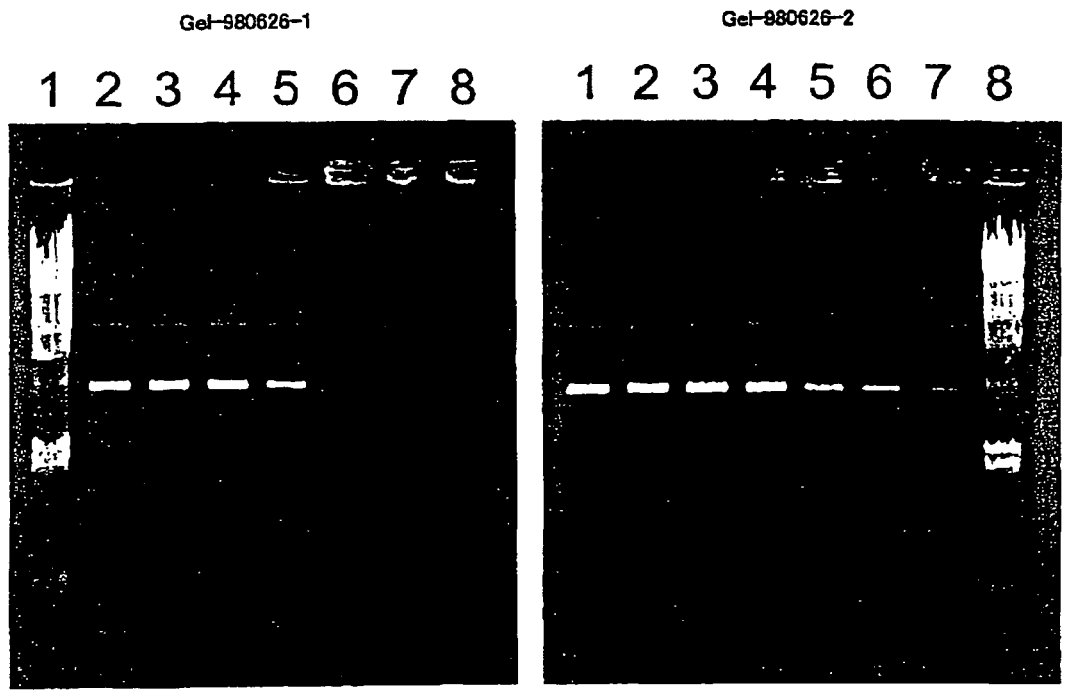

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: antisense
      oligomer

<400> SEQUENCE: 1
ctcgtaggcg ttgtagttgt                                                      20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:
      phosphorothioate antisense oligomer

<400> SEQUENCE: 2
ctcgtaggcg ttgtagttgt                                                      20

```
<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      phosphorothioate sense oligomer

<400> SEQUENCE: 3
gagcatccgc aacatcaaca                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      phosphorothioate scramble oligomer

<400> SEQUENCE: 4
agtcgcatgc acacaacaca                                              20

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:
      phosphorothioate random oligomer

<400> SEQUENCE: 5
gaccatcgtc gattccagt                                               19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      phosphorothioate random oligomer

<400> SEQUENCE: 6
catgaacatc ctgagcatcc                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:
      phosphorothioate random oligomer

<400> SEQUENCE: 7
gttcacgaag aaagaaggct                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:
      phosphorothioate antisense oligomer

<400> SEQUENCE: 8
ctcgtaggcg ttgtagttgt                                              20
```

METHOD OF PROMOTING NUCLEIC ACID TRANSFER

FILED OF THE INVENTION

The present invention belongs to medical field, specifically to gene therapy and genetic fundamental research. More specifically, the invention relates to preparations for facilitating the transfer of a desired nucleic acid into a target cell, and processes therefor.

BACKGROUND ART

Recently, gene therapy has been actively studied, and applied practically to clinical therapy of various cancers and genetic diseases. Gene therapy is an approach to treat a disease by repairing or correcting a defective gene, and comprises transferring a gene encoding an intended enzyme, cytokine, or the like into a cell of a patient, and allowing to produce the intended substance from the gene in the body, thereby treating the disease. Gene therapy is a medication that controls a basis of life, and has a potential to treat various diseases such as AIDS, rheumatoid arthritis, lifestyle-related diseases, in addition to cancers and genetic diseases.

In gene therapy, transfer efficiency of gene into a target cell is an important factor in the increased efficacy of the therapy. Gene therapy for cancers includes therapies by virus such as adenovirus (Cardiovascular Research, 28, 445 (1994); Science, 256, 808 (1992); Gastroenterology, 106, 1076 (1994); TIBTECH, 11, 182 (1993); J. Biol. Chem, 266, 3361 (1991); Nature Medicine, 1, 583 (1995) and the cited references therein) and those by liposome formulations (Biochem Biophys Acta, 1097, 1 (1991); Human Gene Therapy, 3, 399 (1992); Proc. Natl. Acad. Sci. USA, 89, 11277 (1992)). Transfer efficiency of genes is generally higher in therapy using virus vectors than therapy using liposome formulations. However, therapy using virus vectors suffers from a problem that multiple administrations are hardly conducted due to immunological responses to viruses (J. Biol. Chem., 269, 13695(1994), Am. J. Respir. Cell Mol. Biol., 10, 369 (1994)).

On the other hand, since the analysis on the whole human genetic information (human genome) was almost completed, the focus has been shifted to post-genome strategies how to utilize the accumulated human genetic information in the fields of medication and industry. Specifically, examinations on human gene functions, as well as the structures and functions of the proteins encoded by the gene using the analyzed genetic information have been emphasized. Such a post-genome examinations require the expression and the production of proteins, which necessarily involve the transfer of intended genes into cells. Genes to be transferred into host cells by adenovirus vectors and liposome vectors or plasmid DNA vectors are not integrated into the genome of the cells, and are transiently expressed. Such vectors can not accomplish the constitutive expression of the genes, which is important in gene therapy and analysis on gene functions.

DISCLOSURE OF THE INVENTION

Thus, an approach to efficiently transfer a nucleic acid representing a gene into a desired cell, and to express the gene during a long period of time without integration of the gene into chromosome of host cells is expected to provide a great utility.

The inventors of the present application found that collagens have an unexpected action, and created an approach to efficiently transfer a nucleic acid into a desired cell. Specifically, we found that the contact of a collagen and a nucleic acid such as plasmid DNA surprisingly results in the formation of a complex, and the formation of a complex facilitates the transfer of a nucleic acid into a cell and expresses the gene during a long period of time. Although Japanese Patent Publication (kokai) No. 71542/1997 describes formulations containing a gene wherein the gene is comprised in a carrier of a biocompatible material such as a collagen, the formulations are sustained release formulations that gradually releases the gene in a living body.

The invention is based on the newly founded use of a collagen or a collagen derivative.

More specifically, the invention relates to:

(1) A preparation for facilitating the transfer of a nucleic acid into a target cell, which comprises a collagen or a collagen derivative;

(2) A preparation for facilitating the transfer of a nucleic acid into a target cell, which comprises a collagen or a collagen derivative complexed with a desired nucleic acid, preferably a preparation for facilitating the transfer of a nucleic acid, wherein the complex is in a form of particle, more preferably a preparation for facilitating the transfer of a nucleic acid, wherein the major axis of the particle is 300 nm to 300 µm, preferably 300 nm to 100 µm, more preferably 300 nm to 50 µm, even more preferably 300 nm to 30 µm; Specifically, a preparation for facilitating the transfer of a nucleic acid wherein the desired nucleic acid is a plasmid DNA, and wherein the ratio of the number of a collagen molecule or a collagen derivative molecule to the number of a nucleotide monomer of the plasmid DNA in the complex is 1:20 to 1:the number of a nucleotide monomer of the plasmid DNA, preferably 1:50 to 1:the number of a nucleotide monomer of the plasmid DNA, more preferably 1:50 to 1:4000, still more preferably 1:50 to 1:2000, and still more preferably 1:50 to 1:1000, or a preparation for facilitating the transfer of a nucleic acid wherein the nucleic acid is an oligonucleotide, and which the ratio of the number of a collagen molecule or a collagen derivative molecule to the number of a nucleotide monomer of the oligonucleotide in the complex is 1:1 to 1:200, preferably 1:3 to 1:150, more preferably 1:20 to 1:120, and still more preferably 1:50 to 1:120;

(3) A particle of the complex comprising a collagen or a collagen derivative and a desired nucleic acid;

(4) A process for preparing a particle of the complex according to the present invention, which comprises mixing a collagen or a collagen derivative and a desired nucleic acid in a solution comprising an agent that inhibits the formation of collagen association body;

(5) A medical instrument, of which the surface is coated with a particle of the complex according to above (3) or a cell culture instrument, of which the surface is coated with the particle of the complex;

(6) A process for transferring a desired nucleic acid into a target cell or a process for improving the expression level of a desired nucleic acid in a target cell, which comprises using a particle of the complex according to above (3);

(7) A process for examining the function of a gene or a protein in a target cell, which comprises coating a solid surface with a particle of the complex according to above (3) that comprises the gene, a gene encoding the protein, or a nucleic acid inhibiting the expression of the gene or the protein in a cell; culturing the target cell on the solid surface; and examining the expression level of the nucleic acid or the expression level of the gene or the protein in the target cell, or the proliferation ratio or the phenotype of the cell; and (8) A process for screening for a nucleic acid that treats a disease, which comprises coating a solid surface with a particle of the complex according to above (3) that comprises a nucleic acid candidate that inhibits the expression of a gene associated with the disease in a cell; culturing the cell presenting the condition of the disease on the solid surface; and examining the expression level of the gene to be inhibited with each of the nucleic acid candidate, or the proliferation ratio or the phenotype of the cell.

The working examples hereinafter illustrate that the preparations for facilitating the transfer of a nucleic acid according to the present invention improved the transfer efficiency of gene into a target cell as shown to express the nucleic acid in a cell culture system in vitro where the gene expression is not observed by mere plasmid DNA. Further, those examples illustrate that the preparations for facilitating the transfer of a nucleic acid according to the present invention increased the stability of a nucleic acid within a cell as shown to sustain the expression of the nucleic acid during a longer period of time than liposome formulations.

According to the invention, it has been found that a collagen is interacted electrostatically and/or physically with a nucleic acid to form a complex. Thus, it is believed that the sustained expression of a nucleic acid as observed in the working examples would result from the complex formation leading to the increased stability of nucleic acids within cells. This is quite different from the mechanism of the sustained release of gene by collagens that was conventionally understood that a gene encapsulated in collagen matrix is gradually released according to the biological degradation of collagen.

BRIEF DESCRIPTION OF DRAWINGS

FIG. 3 is a photograph substitute for drawing which depicts an agarose-gel electrophoresis showing the effect of heparan sulfate on the electrostatic interaction between plasmid DNA and atelocollagen.

BEST MODE FOR CARRYING OUT THE INVENTION

Figure 1:
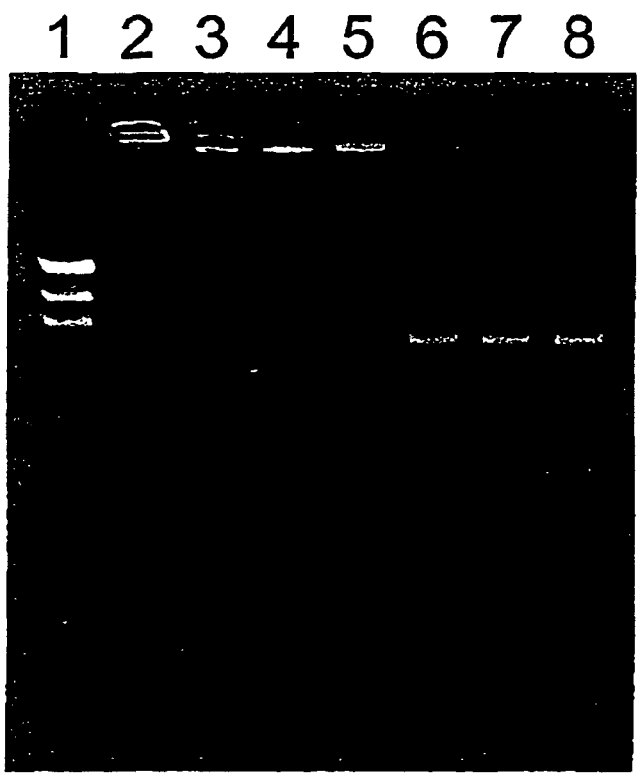
FIG. 1 is a photograph substitute for drawing which depicts an agarose-gel electrophoresis showing the electrostatic interaction between the defined concentration of plasmid DNA and the various concentrations of atelocollagen.

1) A Preparation for Facilitating the Transfer of a Nucleic Acid

As the first embodiment, the invention provides a preparation for facilitating the transfer of a nucleic acid into a target cell, which comprises a collagen or a collagen derivative. The embodiment is based on the effect of a collagen or a collagen derivative on the facilitation of the transfer of a nucleic acid into a target cell, which has been found for the first time. In other words, the present embodiment of the invention provides a new use of a collagen or a collagen derivative to facilitate the transfer of a nucleic acid into a target cell.

As used herein, "a collagen or a collagen derivative" generally means any kind of collages or collagen derivatives as used in medical, cosmetic, industrial, and food fields. A soluble collagen or a solubilized collagen is preferably utilized. Soluble collagens are soluble in an acidic or neutral water or a water containing a salt, whereas solubilized collagens include an enzymatically solubilized collagen which may be solubilized with an enzyme, an alkali-solubilized collagen which may be solubilized with an alkali, both collagens being preferably capable of penetrating through a membrane filter having a pore size of 1 micrometer. Solubility of collagen varies depending on the crosslinking degree of the collagen, and higher is the crosslinking degree, more difficult the collagen is solubilized. Accordingly, the crosslinking degree of a collagen as used in the present invention is, for example, not more than trimer, more preferably not more than dimer. Preferable molecular weight of the collagen is, for example, from about 300,000 to about 900,000, and more preferably from about 300,000 to about 600,000. Collagens as used herein include those extracted from any animal species, and it is desired that preferable collagens are extracted from vertebrates, more preferable collagens are extracted from a mammal, a bird, or a fish, and still more preferable collagens are extracted from a mammal or a bird having a high denaturation temperature. Any type of collagen may be used, and, because of the type existing in animal bodies, type I-V collagens are preferable. For example, such collagens include a type I collagen obtained by acid extraction from a mammal dermis, and, more preferably, they include, for example, a type I collagen obtained by acid extraction from calf dermis, a type I collagen produced by genetic engineering, and the like. Collagens derived from tendon, which are also type I collagens, are not suitable because they have a high degree of crosslinking and are insoluble. Further, an atelocollagen that is obtained by removing enzymatically a telopeptide having a high antigenicity or an atelocollagen produced by genetic engineering is preferable for the sake of safety, and an atelocollagen having three or less tyrosine residues per 1000 residues is more preferable. Alternatively, collagens having a modified side chain, crosslinked collagens or the like may be utilized if desired. Collagens having a modified side chain includes, for example, succinylated collagens and methylated collagens, whereas crosslinked collagens include, for example, collagens treated with glutaraldehyde, hexamethylene diisocyanat, a polyepoxy compound or the like (Fragrance Journal 1989-12, 104-109, Japanese Patent Publication(kokai) No. 59522/1995). Preferred collagen derivatives are a gelatin or a gelatin-crosslinking complex, or a crosslinking complex thereof with a collagen.

Collagens or collagen derivatives may be used in admixture with another biocompatible material. Biocompatible materials include, for example, gelatin, fibrin, albumin, hyaluronic acid, heparin, chondroitin sulfate, chitin, chitosan, alginic acid, pectin, agarose, hydroxyapatite, polypropylenes, polyethylenes, polydimethylsiloxane, and a polymer of glycolic acid, lactic acid or amino acid, and a copolymer thereof, and a mixture containing two or more of those biocompatible materials.

2) A Preparation for Facilitating the Transfer of a Nucleic Acid, which Comprises a Complex As the second embodiment, the present invention provides a preparation for facilitating the transfer of a nucleic acid into a target cell, which comprises a collagen or a collagen derivative and a desired nucleic acid, preferably comprises particles of a complex as an essential component.

Nucleic acids are hardly transferred into cells when administered to the cells in vitro solely in the presence of blood serum. Nucleic acids can be efficiently transferred into cells when formed with a collagen or a collagen derivative into a complex.

As used herein, "a nucleic acid" may be any polynucleotide or any oligonucleotide, and may be any DNA or RNA molecule. DNA molecules include a plasmid DNA, cDNA, a genomic DNA or a synthesized DNA. Both DNA and RNA may be double-stranded or single-stranded. Single-stranded ones include a coding strand and a non-cording strand. As used herein, "a nucleic acid" includes a DNA derivative and an RNA derivative, which derivative means a nucleic acid having a phosphorothioate bond, or a nucleic acid containing an internucleotide having a phosphate, sugar or base moiety chemically modified to avoid enzymatic degradations. As used herein, "a nucleic acid" also includes viruses such as adenovirus and retrovirus.

Preferably, "a nucleic acid" is an oligonucleotide or a ribozyme, and more preferably an oligonucleotide or a ribozyme that is from 5 to 100 mer, more preferably from 5 to 30 mer. It is preferred to utilize a plasmid DNA encoding a protein exhibiting a physiological activity to treat or ameliorate pathological conditions or a plasmid DNA encoding a protein inducing an immunological response to treat or ameliorate pathological conditions.

When the nucleic acid is a vector as used in gene therapy such as a plasmid DNA or a virus, it is preferably a system as constructed to express the encoded genetic information in cells, such as a vector that comprises an element such as a promoter necessary to express an intended gene, or an element capable of integrating into chromosomes. Size of plasmid DNAs as a nucleic acid used herein is not limited, and may be selected appropriately from the sizes that allow the encoded genetic information to be efficiently prepared via genetic engineering, and efficiently expressed in cells to be transferred.

The preparation for facilitating the transfer of a nucleic acid according to the invention may contain a few kinds of separate vectors incorporated with different desired nucleic acids. Further, a vector may comprise many genetic information. Amounts of the vector comprised in the preparation for facilitating the transfer are not limited.

Nucleic acids encoding a protein necessary to be expressed in gene therapy includes any gene capable to be used in the treatment of a genetic disease, which is exemplified by, but is not limited to, a gene encoding an enzyme such as adenosine deaminase, thymidine kinase; a cytokine such as GM-CSF, IL-2; or fibroblast growth factor HST-1 (FGF4). Nucleic acids encoding other proteins necessary to be expressed in gene therapy includes, but is not limited to, a gene aimed at the treatment or the prevention for an infection or a tumor, which encodes a protein or a peptide serving as an antigen to induce immune response, i.e., the gene encoding the protein or the peptide capable of serving as an antigen such as mentioned above, for example, a gene encoding the surface protein HA or NA, or the nuclear protein NP of influenza virus, type C hepatitis virus E2 or NS 1 protein, type B hepatitis virus HBs antigen protein, type A hepatitis virus capsid protein VP1 or VP3 or capsidoid protein, dengue virus Egp protein, RS virus F or G protein, G or N protein of the rabies virus structural protein, herpes virus gD protein, Japanese encephalitis virus E1 or pre-M protein, *rotavirus* coat protein VP7 or coat protein VP4, human immunodeficiency virus gp120 or gp160 protein, *Leishmania major* surface antigen protein, malaria circum sporozoite major surface antigen protein, *Toxoplasma* 54-kd or CS protein, cell surface protein PAc of caries-causing *Streptococcus mutans*; a gene encoding tumor regression antigens such as MAGE-1, MAGE-3, and BAGE, tissue-specific antigens such as tyrosinase, Mart-1, gp100 and gp75, p15, Muc1, CEA, HPV, E6, E7, HPR2/neu, etc.; and the genes which are described in "Immunization with DNA"; Journal of Immunological Methods, vol. 176, 1994, pages 145-152.

In the case that nucleic acids are oligonucleotides, they includes a base sequence, of which at least the portion binds complementarily under physiological condition to a sense or antisense strand of a gene encoding a protein that has a physiological effect to disrupt the homeostasis of a living body, a gene specific to pathogenic viruses, bacteria or the like, and, more specifically, they include a base sequence that binds complimentarily to the messenger RNA of a gene specific to a pathogenic virus, a bacterium or the like, or a gene encoding a protein having a physiological effect to disrupt the homeostasis of a living body.

More specifically, oligonucleotides as used in the present invention includes a sequence complementary to a region containing an initiation codon of a messenger RNA, or to a splicing site of a precursor messenger RNA. Examples of the oligonucleotides as used in the present invention include, for example, those used for treatment or prevention of a cancer, such as an oligonucleotide having a sequence of 5'-CTCG-TAGGCGTTGTAGTTGT-3' (SEQ ID NO: 1) which specifically inhibits the expression of hst-1; ISIS3521 which specifically inhibits the expression of protein kinase $C_\alpha$ to effectively treat progressive cancers such as non-small cell lung carcinoma and colon cancer, and which has been applied in the trials to the treatment of prostate cancer, breast cancer, ovary cancer, pancreas cancer, large intestinal cancer, small cell lung carcinoma; ISIS5132/CGP69846A which specifically inhibits the expression of C-raf kinase and has been applied in the trials to the treatment of prostate cancer, breast cancer, ovary cancer, cephalophyma, pancreas cancer, large intestinal cancer, small cell lung carcinoma; ISIS 2503 which specifically inhibits the expression of Haras and has been applied in the trials to the treatment of large intestinal cancer, breast cancer, cephalophyma, pancreas cancer, and small cell cancer; GEM231 which specifically inhibits the expression of protein kinase A type I; MG98 which specifically inhibits the expression of DNA methyl transferase; INXC-6295 which inhibits the expression of c-myc; INX-3001 which inhibits the expression of c-myb and has been considered to be applied to the treatment of leukemia; G-3139 (Genasense) which inhibits expression of bc1-2 and has been considered to be applied to the treatment of non-Hodgkin's lymphoma, large intestinal cancer, small cell lung carcinoma, chronic lymphatic leukemia, acute myeloid leukemia, breast cancer, lymphoma, melanoma, myeloma, non-small cell lung carcinoma, prostate cancer; an oligonucleotide which inhibits the expression of MDM2 protein; an oligonucleotide which inhibits the expression of VEGF and the like. Further, examples of the oligonucleotides used for treatment or prevention of infectious diseases include GEM92 and GPI-2A which inhibits the growth of HIV. ISIS2922 (fomivirsen), Vitravene, ISIS 13312 and GEM 132 which inhibits the growth of cytomegalovirus, ISIS 14803 which inhibits the growth of hepatitis C virus, and the like. Examples of the oligonucleotides used for treatment of inflammation include ISIS2302 which specifically inhibits the expression of ICAM-1, and which has been applied in the trials to the treatment of Crohn's disease, ulcerative colitis, kidney transplantation rejection inhibition, psoriasis, asthma; EPI-2000 which inhibits the expression of adenosine A1 receptor and has been applied in the trials to the treatment of asthma; and oligonucleotides which inhibit the expression of TNF-$\alpha$, CD49d (VLA-4), VCAM-1, PECAM-1 and the like. Further, examples of the oligonucleotides that prevent the restenosis after percutaneous transluminal coronary angiogenesis include Resten-NG that inhibits the expression of c-myc.

Genes encoding a protein that exhibits a physiological effect to disrupt the homeostasis include, for example, a series of genes, so-called cancer genes. Specifically, they include genes for growth factors, receptor type tyrosine kinases, non-receptor type tyrosine kinases, GTP-binding proteins, serine-threonine kinases, transcription factors and the like. More specifically, they include genes coding for hst-1 or ornithine decarboxylase and the like.

The preparation for facilitating the transfer of a nucleic acid according to the present invention may further comprise a pharmaceutically acceptable additive as appropriate in addition to the complex of the present invention. Pharmaceutically acceptable additives include an agent making isotonic, a pH modifier, and a soothing agent in case of the use of the complex as injection, and an excipient, a disintegrator, and a coating agent in case of the use of the complex as solid, as well as those described in Japanese Handbook of Pharmaceutical Excipients (Japan Pharmaceutical Excipients Council). Specific examples include salts and saccharides, which are used to keep the pH 6-8, or to make isotonic with cells.

The preparation for facilitating the transfer of a nucleic acid according to the present invention may be in a form of solid or solution. The preparation in a form of solid is loaded to a desired cell as it is, or after making a solution with a purified water, a physiological solution, a buffer isotonic with living bodies, or the like. Such preparation in a solution form also constitutes a part of the present invention.

The administration of the preparation for facilitating the transfer of a nucleic acid according to the present invention may be selected from oral route, injection, eye drop, nasal drop, transpulmonary route, transdermal absorption, and oral route and injection are preferred. The preparation may be administered to various sites depending on diseases, and may be placed on the necessary site at the time of operation.

In the present embodiment, the invention provides:
(1) A preparation for facilitating the transfer of a nucleic acid into a target cell, which comprises as an essential component a complex, preferably particles of a complex comprising a desired nucleic acid and a collagen or a collagen derivative, wherein the major axis of the particle is preferably 300 nm to 300 μm, more preferably 300 nm to 100 μm, even more preferably 300 nm to 50 μm, still more preferably 300 nm to 30 μm;
(2) The preparation for facilitating the transfer of a nucleic acid according to (1) wherein the target cell is an animal cell;
(3) The preparation for facilitating the transfer of a nucleic acid according to (2) wherein the target cell is an organ or a tissue which requires to be treated, or its cell around;
(4) The preparation for facilitating the transfer of a nucleic acid according to any one of (1) to (3) wherein the collagen is atelocollagen:
(5) The preparation for facilitating the transfer of a nucleic acid according to any one of (1) to (4) wherein the molecular weight of the collagen is from about 300,000 to about 900,000;
(6) The preparation for facilitating the transfer of a nucleic acid according to any one of (1) to (5) wherein the collagen derivative is a gelatin or a gelatin-crosslinking complex;
(7) The preparation for facilitating the transfer of a nucleic acid according to any one of (1) to (5) wherein the collagen derivative is a collagen-crosslinking complex;
(8) The preparation for facilitating the transfer of a nucleic acid according to any one of (1) to (7) wherein the nucleic acid is an oligonucleotide;
(9) The preparation for facilitating the transfer of a nucleic acid according to (8) wherein the oligonucleotide is from 5 to 30 mer in length;
(10) The preparation for facilitating the transfer of a nucleic acid according to (8) or (9) wherein the oligonucleotide is a DNA or a DNA derivative;

(11) The preparation for facilitating the transfer of a nucleic acid according to (8) or (9) wherein the oligonucleotide is an RNA or an RNA derivative;

(12) The preparation for facilitating the transfer of a nucleic acid according to (10) or (11) wherein the DNA derivative or the RNA derivative has at least one phosphorothioate bond;

(13) The preparation for facilitating the transfer of a nucleic acid according to any one of (1) to (7) wherein the nucleic acid is a ribozyme or an oligonucleotide;

(14) The preparation for facilitating the transfer of a nucleic acid according to any one of (1) to (7) wherein the nucleic acid is a plasmid DNA;

(15) The preparation for facilitating the transfer of a nucleic acid according to (13) wherein the plasmid DNA encodes a protein that exhibits a physiological activity to treat or ameliorate pathological conditions;

(16) The preparation for facilitating the transfer of a nucleic acid according to (13) wherein the plasmid DNA encodes a protein that induces an immunological response to treat or ameliorate pathological conditions;

(17) The preparation for facilitating the transfer of a nucleic acid according to (1) to (16) wherein the preparation is in a form of solution, and the complex comprises 10 mg/ml or less of a nucleic acid;

(18) The preparation for facilitating the transfer of a nucleic acid according to (17) wherein the complex comprises 1 mg/ml or less of a nucleic acid;

(19) The preparation for facilitating the transfer of a nucleic acid according to (18) wherein the complex comprises 500 µg/ml or less of a nucleic acid;

(20) The preparation for facilitating the transfer of a nucleic acid according to (1) to (19) wherein the preparation has pH5 to pH9, preferably, pH6 to pH8;

(21) The preparation for facilitating the transfer of a nucleic acid according to (1) to (20) further comprising phosphoric acid in a concentration from 0.001M to 0.1M;

(22) The preparation for facilitating the transfer of a nucleic acid according to (21) further comprising phosphoric acid in a concentration from 0.01M to 0.1M;

(23) The preparation for facilitating the transfer of a nucleic acid according to (1) to (22) further comprising an agent that inhibits the formation of collagen association body, for example sucrose or arginine; and

(24) The preparation for facilitating the transfer of a nucleic acid according to (1) to (24) further comprising an appropriate amount of a pharmaceutically acceptable additive.

3) Complexes

As the third embodiment, the present invention provides a complex comprising a collagen or a collagen derivative and a desired nucleic acid. The complexes include electrostatic complexes that are bound and formed by the electrostatic force, and physical complexes that are bound and formed by the physical force such as hydrophobic binding. Both binding systems may coexist, and this embodiment is also fallen in the scope of the present invention.

It has been found for the first time that a collagen is electrostatically interacted with a nucleic acid to form a complex.

As used herein, "electrostatic complexes" means polyionic complexes between a collagen or a collagen derivative having many electric charges in the molecule and a nucleic acid, and specifically means binding bodies wherein a collagen or a collagen positively charged electrically attract to a nucleic acid negatively charged. In the polyionic complexes, many counter ions are released from the molecule on the complex formation, and therefore very large increase in entropy is produced. In view of the formation of such electrostatic complexes, it is understood that the sustained expression of a nucleic acid as observed in the working examples would result from the complex formation leading to the increased stability of nucleic acids within cells.

Minimum unit of the complex of the present invention is a complex formed by one molecule of collagen and one molecule of nucleic acid. We found that a collagen forms a complex with a nucleic acid, and stimulatingly associates with another collagen to form an association body. The association body is formed in a manner that a collagen molecule having a cylindrical shape wherein the major axis is about 300 nm and the diameter is 1.5 nm is predominantly associated parallel to the longitudinal axis of the molecule. Accordingly, the complexes are formed by the noncovalent binding between many association bodies and many nucleic acid molecules, and include filamentous complexes having a longitudinal axis of 1 nm or more as a result of the largely developed extension of the bodies, filamentous complexes wherein fine bodies are each bound via nucleic acids, and particulate complexes formed by more fine complexes and nucleic acids.

The complexes of the present invention can be various in shape.

The complexes of the present invention are preferably in a form of particle. As used herein "particle" means a shape that a collagen or a collagen derivative could assume, and does not necessarily mean a spherical shape. Minimum size of the complexes of the present invention is 300 nm that corresponds to the major axis of a complex formed by one molecule of collagen. The particles have a major axis of 300 nm to 1 mm, and in view of transfer efficiency of nucleic acids, they preferably have a major axis of 300 nm to 300 µm, more preferably 300 nm to 100 µm, even more preferably 300 nm to 50 µm, still even more preferably 300 nm to 30 µm.

We found that the ratio of a collagen or a collagen derivative to a nucleic acid composed in a complex is responsible for the fact that the complex can assume various forms or shapes, and that the form of the complex is dependent exclusively on the development of the association (fibrosis) of the collagen or collagen derivative promoted by the formation of the complex with the nucleic acid. We also found that the excess formation of the association bodies is not suitable for the transfer of the nucleic acid, and found that the form or the shape of the complex could be controlled by adjusting the concentration of the collagen or collagen derivative and the desired nucleic acid to be mixed, as well as environmental factors such as salt concentration, temperature, pH, and glucose concentration. Further, we observed that a plasmid DNA having 1000 bp or more is extremely promoted in the association, whereas a plasmid DNA having a 100 bp or less is weakly promoted in the association, and found that the association of collagen or collagen derivative involved in the complex formation is affected by the length of the nucleic acid, concluding that there is a composition of a collagen or collagen derivative and a nucleic acid optimal for the association depending on the length of the nucleic acid.

The form of the shape of the complex may affect the transfer efficiency of nucleic acids into cells. The finding that collagens are complexed with nucleic acids, and the shape of the complex affects the transfer efficiency and the expression efficiency of nucleic acids in cells provides a strategy for optimizing the transfer efficiency of nucleic acids. Liposomes as used in laboratory to transfer nucleic acids into target cells are difficult to be widely utilized from practical view points, since they tend to aggregate together immediately when combined with nucleic acids, are varied in transfer efficiency on use, and are necessarily prepared just before use. However, the complexes of the present invention are stable in the form or the shape when stored in cold space. The most important issue in gene transfer technique is that widely used methods are quite few. The complexes of the present invention are stable in the form or the shape and could be used practically.

In the present embodiment, the invention provides:

(1) A particle of the complex comprising a desired nucleic acid and a collagen or a collagen derivative;
(2) The particle of the complex according to (1), wherein the major axis is 300 nm to 300 μm;
(3) The particle of the complex according to (2), wherein the major axis is 300 nm to 100 μm;
(4) The particle of the complex according to (3), wherein the major axis is 300 nm to 50 μm, preferably 300 nm to 30 μm;
(5) The particle of the complex according to (1) to (4), wherein the nucleic acid is an plasmid DNA;
(6) The particle of the complex according to (5), wherein the ratio of the number of a collagen molecule or a collagen derivative molecule to the number of a nucleotide monomer of the plasmid DNA is 1:20 to 1:the number of a nucleotide monomer of the plasmid DNA, preferably 1:50 to 1:the number of a nucleotide monomer of the plasmid DNA, more preferably 1:50 to 1:4000, even more preferably 1:50 to 1:2000, still even more preferably 1:50 to 1:1000;
(7) The particle of the complex according to (6), wherein the ratio is 1:96 to 1: the number of a nucleotide monomer of the plasmid DNA;
(8) The particle of the complex according to (7), wherein the ratio is 1:96 to 1:1122;
(9) The particle of the complex according to (8), wherein the ratio is 1:96 to 1:701;
(10) The particle of the complex according to (1) to (4), wherein the nucleic acid is an oligonucleotide;
(11) The particle of the complex according to (10), wherein the ratio of the number of a collagen or a collagen derivative to the number of a nucleotide monomer of the oligonucleotide in the complex is 1:1 to 1:200, preferably 1:3 to 1:150, more preferably 1:3 to 1:120;
(12) The particle of the complex according to (11), wherein the ratio is 1:20 to 1:120;
(13) The particle of the complex according to (12), wherein the ratio is 1:50 to 1:120;
(14) The particle of the complex according to (1) to (13), which is comprised in a solution of pH 5 to pH 9, preferably pH 6 to pH 8;
(15) A process for preparing a particle of the complex according to (1) to (13), which comprises mixing a collagen or a collagen derivative and a desired nucleic acid in a solution cooled to 10° C. or less;
(16) A process for preparing a particle of the complex according to (1) to (13), which comprises mixing a collagen or a collagen derivative and a desired nucleic acid in a solution comprising phosphoric acid in a concentration from 0.001M to 0.1M;
(17) A process for preparing a particle of the complex according to (1) to (13), which comprises mixing a collagen or a collagen derivative and a desired nucleic acid in a solution comprising phosphoric acid in a concentration from 0.01M to 0.1M;
(18) A process for preparing a particle of the complex according to (1) to (13), which comprises mixing a collagen or a collagen derivative and a desired nucleic acid in a solution comprising an agent that inhibits the formation of collagen association body, for example sucrose or arginine;
(19) A process for preparing a particle of the complex according to (1) to (13), which comprises mixing a collagen or a collagen derivative and a desired nucleic acid in a solution comprising an appropriate amount of a pharmaceutically acceptable additive wherein the pharmaceutically acceptable additive is as defined above;
(20) A process for preparing a particle of the complex according to (1) to (13), which comprises combining two or more of the processes according to (14) to (19);
(21) A process for preparing a particle of the complex according to (1) to (13), which further comprises penetrating the complex through a filter having a pore size of 100 μm or less for size selection.
(22) The process according to (21), which comprises penetrating the complex through a filter having a pore size of 10 μm or less for size selection;
(23) A process for preparing a particle of the complex according to (1) to (13), which further comprises centrifuging the complex at 10,000 rpm or more for concentration and isolation;
(24) The process according to (23), which comprises centrifuging the complex at 50,000 rpm or more.

As used herein, "the number of a nucleotide monomer" means the number of nucleotide monomer units composing a desired nucleic acid. As used herein, "the ratio of the number of a collagen molecule or a collagen derivative molecule to the number of a nucleotide monomer" means the number of nucleotide monomers in a desired nucleic acid relative to one molecule of a collagen or collagen derivative comprising an electrostatically or physically bound complex. The number of nucleotide monomers is almost the same as "negative charge of a desired nucleic acid". As used herein, "negative charge of a desired nucleic acid" means the number of phosphate groups intervening between nucleotides composing a nucleic acid. The numeral values of the negative charge of nucleic acid is equal to the number of phosphate groups of the nucleic acid, phosphate groups intervening between nucleotides, and phosphorus-containing groups intervening between nucleotides (phosphate groups and phosphorothioate groups).

As used herein, "an agent that inhibits the formation of collagen association body" includes an agent that inhibits electrostatic interactions that would cause the formation of collagen association body via charges of basic and acidic amino acids comprised mainly in a collagen molecule, and an agent that inhibits the ordered arrangement of collagen molecules. Examples of the former include salts amino acids, and urea, and examples of the latter include saccharides such as sucrose, and arginine.

The particle of the complex according to the invention may be comprised in the preparation for facilitating the transfer of a nucleic acid according to the invention.

4) Medical Instruments and Cell Culture Instruments

As the fourth embodiment, the invention provides a medical instrument or a cell culture instrument, of which the surface is coated with a particle of the complex according to the present invention.

It has been found that the transfer efficiency of a nucleic acid is improved when a particle of the complex according to the present invention is coated onto a solid surface, and target cells are contacted thereto, compared to dropwise addition of a particle of the complex according to the present invention to the target cells, in other words, solid coating of the complex particles is superior to dropwise addition in terms of transfer efficiency (as shown in Example 6).

Specifically, medical instruments and cell culture instruments according to the present embodiment include artificial vascular grafts, medical stents, and artificial hearts. Artificial vascular grafts are required to allow vascular endothelial cells to proliferate and spread in their inner side in order to inhibit fibrin development and suppress the complement activation within the vessels. Thus, when coated onto artificial vascular grafts, a particle of the complex according to the present invention wherein nucleic acids encoding endothelial growth factors such as a vascular endothelial growth factor (VEGF) are bound to a collagen is expected to readily and rapidly proliferate vascular endothelial cells.

Cell culture instruments, of which the surface is coated with a particle of the complex comprising a desired nucleic acid and a collagen or a collagen derivative include plates, flasks, 96-well microplates as usually used in cell culture experiments. Example 6 hereinafter demonstrated that amounts of the complex particles coated onto the solid surface per unit area drastically affect transfer efficiency of nucleic acids into cells. Accordingly, the amounts of the complex particles coated onto the solid surface per unit area constitute a part of the present invention.

In the present embodiment, the invention specifically provides:

(1) A medical instrument or a cell culture instrument that is coated with a particle of the complex comprising a desired nucleic acid and a collagen or a collagen derivative;

(2) The medical instrument or the cell culture instrument according to (1), wherein the particle of the complex is coated so that an amount from 0.1 µg to 50 µg of a nucleic acid is comprised in 1 square centimeter;

(3) The medical instrument or the cell culture instrument according to (1), wherein the particle of the complex is coated so that an amount from 0.1 µg to 50 µg of a nucleic acid is comprised in 1 square centimeter;

(4) The medical instrument or the cell culture instrument according to (3), wherein the particle of the complex is coated so that an amount from 1 µg to 10 µg of a nucleic acid is comprised in 1 square centimeter;

(5) The medical instrument or the cell culture instrument according to (1), wherein the particle of the complex having a major axis of 300 nm to 300 µm is released from the solid surface when exposed in a solution isotonic with a living body; and (6) The medical instrument or the cell culture instrument according to (5), wherein the solution isotonic with a living body is a phosphate buffer comprising sodium chloride.

Feasible distribution of the invention on the market is important to carry out the present embodiment. As described above, liposomes are required to be prepared just before use, meaning extremely poor distribution. In general, it is believed difficult to distribute adenovirus as coated onto the solid surface according to the present embodiment. However, it has been found unexpectedly that adenovirus as coated and dried on solid surface together with a collagen according to the present invention retain the infectivity at room temperature for 7 days. This shows that the medical instrument and the cell culture instrument according to the invention could be feasibly distributed on the market.

5) A Process for Transferring a Desired Nucleic Acid into a Target Cell or a Process for Improving the Expression Level of a Desired Nucleic Acid in a Target Cell As described above, a particle of the complex according to the present invention can be used to facilitate the transfer of a desired nucleic acid into a target cell. Thus, as the fifth embodiment, the present invention provides a process for transferring a desired nucleic acid into a target cell or a process for improving the expression level of a desired nucleic acid in a target cell, which comprises using a particle of the complex according to the present invention. As used herein, "improving the expression level" means the increasing of the expression level of a desired nucleic acid or the extension of the duration time of the expression.

Thus, in the present embodiment, the invention provides:

(1) A process for transferring a desired nucleic acid into a target cell, which comprises using a particle of the complex as defined above comprising a desired nucleic acid and a collagen or a collagen derivative;

(2) A process for improving the expression level of a desired nucleic acid in a target cell, which comprises using a particle of the complex as defined above comprising a desired nucleic acid and a collagen or a collagen derivative;

(3) The process according to (2), wherein the process is to improve the expression level, or to extend the duration time of the expression;

(4) The process according to any one of (1) to (3), wherein the particle of the complex as defined above is coated onto the solid surface, and the target cell is cultured on the solid surface.

6) A Process for Examining the Function of a Gene or a Protein in a Target Cell

According to the present invention wherein the transfer of a nucleic acid into a cell is facilitated, it is possible to readily examine the function of a gene or a protein in a target cell. For example, human genome project identify a large number of genes, and showed the base sequences thereof. It is necessary to clarify the functions of identified genes in order to utilize those information practically in the field of medication or food industry. However, it has been clear that the conventional approach to examine the function by producing and purifying proteins from genes one by one is time-consuming and not practical. Accordingly, a process for examining the function of a gene which comprises transferring and expressing a plasmid DNA incorporated with a gene to be examined into a cell, or a process for examining the function of a gene which comprises transferring an antisense oligonucleotide that inhibits the expression of a gene to be examined into a cell and inhibiting the gene expression should be useful. In case of the examination of the gene function by phenotype of the cell as shown above, it is necessary to conduct the process for transferring a plasmid DNA or an antisense DNA into a cell without adverse affection to the cell as much as possible. Thus, a liposome, which is high in cytotoxicity, would affect the information as obtained due to its cytotoxicity. On the other hand, a collagen as used herein hardly affect the cells since a collagen originally exist in a living body and contacts with the cells, and therefore the invention enables the measurement of gene functions without noise. Particular measurements comprise mixing a plasmid DNA or an adenovirus expressing a gene to be examined, or an antisense oligonucleotide inhibiting the expression of a gene to be examined, allowing the formation of particles of the complex, then coating and arranging the same on the solid surface of the culture plate. Solid plates as used herein include 96-well multiwell-plates and microplates. After the coated complex particles are dried and immobilized on the solid, cells are seeded and cultured on the plate for several days. The coated complex particles are transferred efficiently into cells attached to the coated part, and allow the expression of a gene to be examined or the inhibition of the same for a long period of time. After a few days, the functions of target genes can be clarified by examining the morphology of the cells, the level of the gene expression in the cells, or the kinds or the amounts of the proteins produced by the cells. The features of the present invention also include selective and efficient transfer of the complex particles coated onto the solid into the cells attached to the coated part. In other words, it is possible to examine the functions of a large number of genes on microplates at a time without comparting of the cells by wells.

In the present embodiment, the invention provides:
(1) A process for examining the function of a gene or a protein in a target cell, which comprises coating a solid surface with a particle of the complex according to above (3) of the present invention that comprises the gene, a gene encoding the protein, or a nucleic acid inhibiting the expression of the gene or the protein in a cell; culturing the target cell on the solid surface; and examining the expression level of the nucleic acid or the expression level of the gene or the protein in the target cell, or the proliferation ratio or the phenotype of the cell;
(2) The process according to (1), wherein the gene or a nucleic acid encoding the protein is a plasmid DNA, and the expression level of the nucleic acid is examined; and
(3) The process according to (1), wherein the gene or a nucleic acid that inhibits the expression of the protein in a cell is an antisense oligonucleotide or a ribozyme, and the expression level of the gene or the protein is examined.

7) A Process for Screening for a Nucleic Acid that Treats a Disease

According to the present invention wherein the transfer of a nucleic acid into a cell is facilitated, it is possible to screening for a nucleic acid that is capable to compensate normal genes, repair or correct defective genes so as to treat various diseases such as genetic diseases, cancers, AIDS, rheumatoid arthritis, lifestyle-related diseases. For example, after the complex particles are formed with a nucleic acid that is examined for a therapeutic effect on diseases and a collagen, and are coated, dried and immobilized on the solid as described in 6) above, cells presenting pathological condition are cultured on the plate, transferring efficiently the nucleic acid into the cell presenting pathological condition. Effects of the nucleic acid may be examined on the basis of change in the morphology of the cells, cell death, cell proliferation, pattern of the gene expression in the cells, or the kinds or the amounts of the proteins produced by the cells. It is evident that, in the nucleic acid transfer in the embodiment, affection by vectors to be transferred should be minimized, and a collagen as used herein makes it possible to examine the effect on pathological condition without noise. The features of the present invention also include coincidental examinations of a large number of genes, as shown by the fact that nucleic acids that is to be examined for function can be immobilized and arranged on a cell culture solid carrier having a tiny area.

In the present embodiment, the invention provides:
(1) A process for screening for a nucleic acid that treats a disease, which comprises coating a solid surface with a particle of the complex according to the present invention that comprises a nucleic acid candidate that inhibits the expression of a gene associated with the disease in a cell; culturing the cell presenting the condition of the disease on the solid surface; and examining the expression level of the gene to be inhibited with each of the nucleic acid candidate, or the proliferation ratio or the phenotype of the cell;
(2) A process for examining a therapeutic effect of a nucleic acid to be expected to inhibit the expression of a gene associated with a disease, which comprises coating a solid surface with a particle of the complex according to the present invention that comprises the nucleic acid; culturing the cell presenting the condition of the disease on the solid surface; and examining the expression level of the gene, or the proliferation ratio or the phenotype of the cell;
(3) The process according to (1) or (2), wherein the nucleic acid is to inhibit the expression of the gene associated with the disease in the cell, or to have a function that inhibits the expression of the gene associated with the disease in the cell; and
(4) The process according to (3), wherein the nucleic acid that inhibits the expression of the gene associated with the disease in the cell is a plasmid DNA encoding the gene, or the nucleic acid that have a function that inhibits the expression of the gene associated with the disease in the cell is an antisense oligonucleotide or a ribozyme.

8) Other Embodiments

In the present embodiments, the invention provides:
(1) A cell culture instrument, of which the surface is coated with a desired nucleic acid together with a collagen or a collagen derivative; preferably the cell culture instrument wherein the desired nucleic acid is complexed with the collagen or the collagen derivative to form a particle of the complex;
(2) A cell culture instrument, of which the surface is coated with a film comprising a collagen or a collagen derivative containing a desired nucleic acid; preferably the cell culture instrument wherein the desired nucleic acid is complexed with the collagen or the collagen derivative to form a particle of the complex;
(3) A cell culture instrument, on which the surface is coated with a film comprising a collagen or a collagen derivative, and a desired nucleic acid;
(4) The cell culture instrument according to (1) to (3), wherein the nucleic acid constitutes a library;
(5) The cell culture instrument according to (4), wherein the nucleic acid is a cDNA or oligonucleotide that constitutes a library;
(6) The cell culture instrument according to (4) or (5), wherein the nucleic acid that constitutes a library is comparted each other at a distance;
(7) A film comprising a collagen or a collagen derivative and a desired nucleic acid wherein the nucleic acid that constitutes a library is comparted each other at a distance; preferably the film wherein the nucleic acid is complexed with the collagen or the collagen derivative to form a particle of the complex;
(8) The film according to (7), wherein the nucleic acid is a cDNA or oligonucleotide that constitutes a library;
(9) The cell culture instrument according to (2) or (3), on which the surface is coated with the film according to (7) or (8);
(10) The cell culture instrument according to (9), that is used for the expression of proteins;
(11) The cell culture instrument according to (9), that is used for the inhibition of gene expression;
(12) A process for examining the function of a gene in a cell, which comprises culturing the cell on the cell culture instrument according to (1) to (6) on which a nucleic acid containing a cDNA of the gene is immobilized; and examining the proliferation ratio or the phenotype of the cell, or the production level of certain proteins;

(13) A process for examining the function of a gene in a cell, which comprises culturing the cell on the cell culture instrument according to (1) to (6) on which an oligonucleotide containing a base sequence complementary to a messenger RNA of the gene is immobilized; and examining the proliferation ratio or the phenotype of the cell, or the production level of certain proteins; and

(14) The cell culture instrument according to (1) to (6), wherein the surface of the cell culture instrument outside the part immobilized by the nucleic acid is hydrophilic or hydrophobic as high as the cell is not attached;

In order to transfer a nucleic acid into a target cell on solid phase, the cell may be cultured on a cell culture instrument, on which a desired nucleic acid together with a collagen or a collagen derivative, or a desired nucleic acid complexed with the collagen or the collagen derivative to form a particle of the complex is directly immobilized. Alternatively, target cells may be cultured on a cell culture instrument, of which the surface is covered with a film comprising a collagen or a collagen derivative containing a desired nucleic acid, or a film comprising a particle of the complex, and a film made of agarose and albumin comprising a collagen or a collagen derivative containing a desired nucleic acid, or a particle of the complex may be used.

The present invention comprises making a library that is constituted with various nucleic acids complexed with a collagen or a collagen derivative independently on the solid phase, and makes it possible to examine the functions of the gene in cells at the same time and in the same condition. Further, the invention provide a library for gene expression or a library for inhibition of gene expression wherein a nucleic acid or an oligonucleotide comprising the libraryed cDNA is arranged on the solid phase, allowing the examination of the gene functions at a stage of cell. Nucleic acids comprising the cDNA that constitutes a library are not limited to a specific species, and include Gene Storm pcDNA3.1 vector (In Vitrogen, Inc.).

When a complex comprising a nucleic acid is arranged on the solid phase, and cells are cultured thereon to examine the functions of the transferred gene, it is necessary to avoid the contamination of the cells, each of which is transferred with respective nucleic acid independently arranged.

The features of the present invention also include selective and efficient transfer of the complex particles coated onto the solid into the cells attached to the coated part. In other words, it is possible to examine the functions of a large number of genes on microplates at a time without comparting of the cells by wells. To do so, wells may be used to compart each part arranged by the nucleic acids, and 6 to 384 wells may compart one plate. In addition to the wells, alternatively, surface on the solid phase that is hydrophilic or hydrophobic as high as the cell is not attached may be used to prevent the cells from moving across the parts arranged by the nucleic acids. As used herein, the surface that is highly hydrophilic means surface having a water-contact angle of 40 degree or less, and the surface that is highly hydrophobic means surface having a water-contact angle of 110 degree or more. Distance between the arranged nucleic acids should be kept over the length of the most extension of the seeded cells. Thus, when the surface of the cell culture instrument outside the part immobilized by the nucleic acid or the part coated with a film comprising a nucleic acid, it is not necessary to carry out culture by comparting the cells with wells, and it is possible to examine the functions of a large number of the genes on a microplate.

EXAMPLES

The present invention is further illustrated by the following Examples and Experiments, but is not restricted by these Examples and Experiments in any way.

Example 1

Formation of Complexes Between a Plasmid DNA and a Collagen

Both equal amounts of an aqueous solution containing a plasmid DNA (pCAHST-1:7.9 Kbp) incorporated with a gene of fibroblast growth factor HST-1 (FGF4) gene (Proc. Natl. Acad. Sci. USA, 84, 2890-2984 (1987)) at 10 μg/ml, and of a neutral aqueous solution containing 200, 60, 20, 6, 2, 0.6, and 0 μg of an atelocollagen (KOKEN CO., LTD.) were mixed together, and the mixtures were analyzed on agarose gel electrophoresis. Agarose gel electrophoresis was carried out with 0.8% agarose gel in TAE (Tris-acetate) buffer at Horizontal Electrophoresis Unit (Mupid, Advance CO.). After electrophoresis, the gel was stained with ethidium bromide, and photographed with a transilluminator. The results are shown in FIG. 1. pCAHST-1 in the presence of the collagen at 10 μg/ml or more did not electrophorese, and retained on the well. This means that pCAHST-1 at 5 μg/ml was complexed with the collagen at 10 μg/ml.

Figure 2:
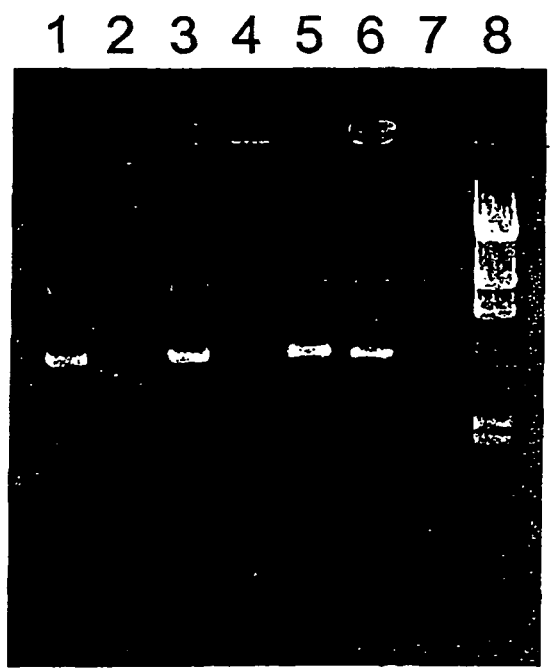
FIG. 2 is a photograph substitute for drawing which depicts an agarose-gel electrophoresis showing the effect of sodium chloride on the electrostatic interaction between plasmid DNA and atelocollagen.

Similarly, both equal amounts of 10 μg/ml pCAHST-1 and 100 μg/ml collagen were mixed together in 10 mM Tris hydrochloride buffer (pH7.5) containing 1.0 M sodium chloride, and the mixture was electrophoresed, which results are shown in FIG. 2. When 1.0 M sodium chloride coexisted, pCAHST-1 irrespective of the presence of the collagen at 100 μg/ml did electrophorese. This means that a complex formed by pCAHST-1 and the collagen should be an electrostatic one.

Further, the formation of a complex between 10 μg/ml pCAHST-1 and the collagen in 10 mM Tris hydrochloride buffer (pH7.5) containing 1.0 M sodium chloride was compared between the presence and the absence of heparan sulfate. The results are shown in FIG. 3. In the absence of heparan sulfate, all of 5 μg/ml pCAHST-1 were complexed with 100 μg/ml collagen, whereas in the presence of heparan sulfate, it found that there were some pCAHST-1 that were not complexed with collagen even at 300 μg/ml. This means that heparan sulfate having a negative charge similar to pCAHST-1 cause the competition in complex formation with the collagen between pCAHST-1 and heparan sulfate, suggesting that pCAHST-1 and a collagen form a electrostatic complex.

Example 2

Microscopy of Complexes

Figure 4:
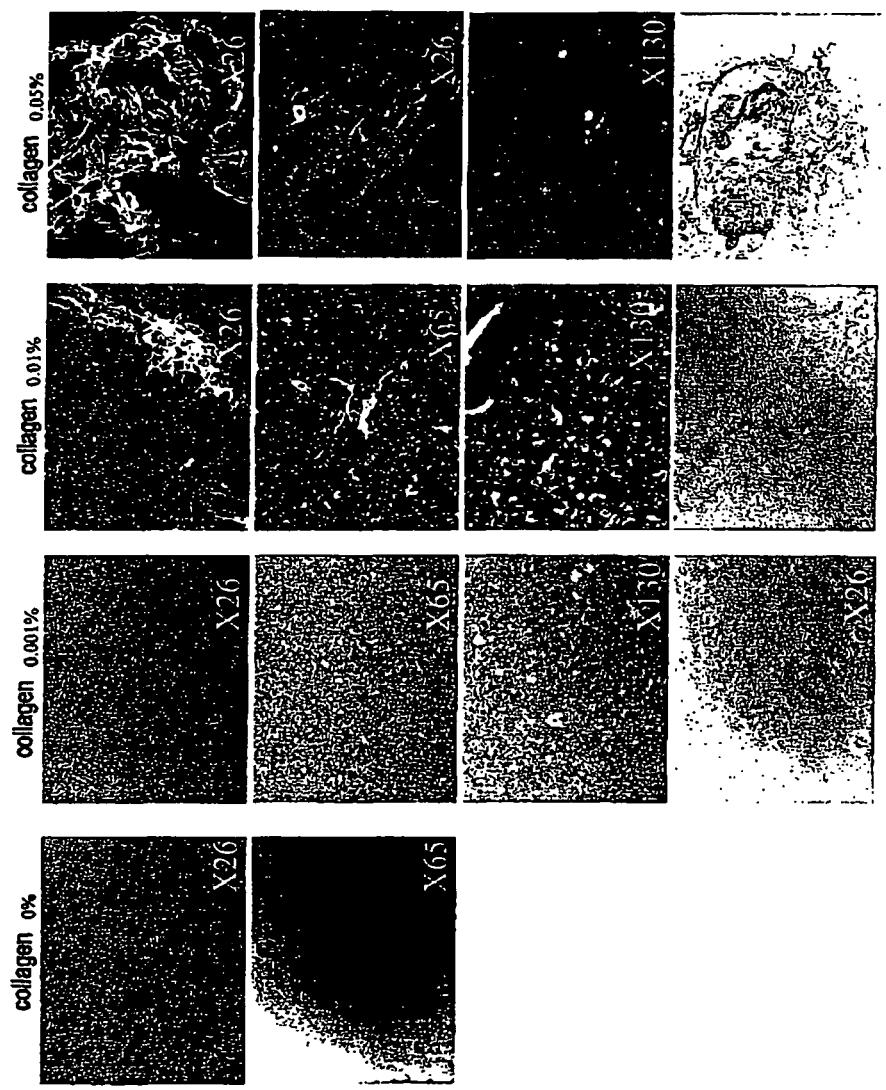
FIG. 4 is a micrograph showing a form of the complexes between plasmid DNA and atelocollagen in various concentrations.
Figure 5:
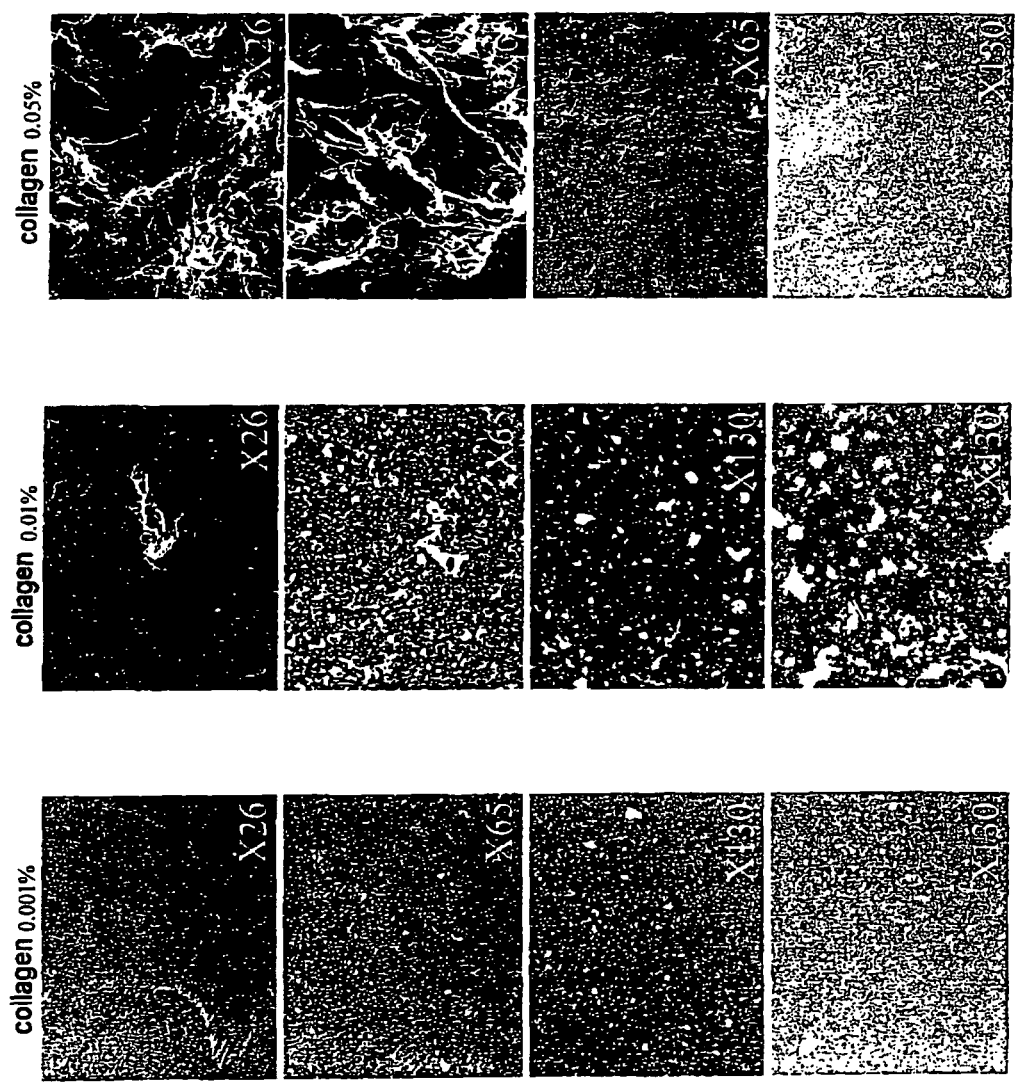
FIG. 5 is a micrograph showing a form of the complexes between plasmid DNA and atelocollagen in various concentrations that were stored for a week.

Both equal amounts of an aqueous solution containing pCAHST-1 at 200 μg/ml, and an aqueous solution containing an atelocollagen at 0, 20, 200, and 1000 μg/ml were mixed, and the mixture was added with PicoGreen dsDNA Quantitation Reagent (Molecular Probes) to stain pCAHST-1 and observed by microscopy. The results are shown in FIG. 4. In case that the collagen concentration after the mixing is 500 μg/ml (0.05% collagen in the figure), the filamentous complexes having a major axis of more than 1 mm were predominantly observed, whereas the particulate complexes having a major axis of 10 to 100 μm were predominantly observed in case that the collagen concentration is 100 μg/ml (0.01% collagen in the figure), and the particulate complexes having a major axis of 10 μm or less were predominantly observed in case that the collagen concentration is 10 μg/ml (0.001% collagen in the figure). This means that the formation of the complexes can be controlled by the concentrations of plasmid DNAs and collagens at the time of mixing. These complexes maintained stably their shape over a week or more when stored at 5° C. (FIG. 5). This means that the complexes can be stored for a long period of time, and be distributed on the market at they are, not requiring the preparation just before use.

Example 3

Extension Effect of Complexes on the Expression Duration Time

Both equal amounts of an aqueous solution containing a plasmid DNA encoding a fluorescent protein (EGFP) (pCMV-EGFP/pEGFP-N1, Clontech Co.) at 200 μg/ml, and an aqueous solution containing an atelocollagen at 0.02%(w/w) were mixed together to prepare a formulation in a gel form.

To human embryonic kidney cells, 293 cells cultured on a dish (diameter: 6 cm), 100 μl of the gel formulation (containing 10 μg of pCMV-EGFP) was added in the presence of 2 ml of serum-free medium. Then, after cultured at 37° C. overnight, the cells were washed with PBS to remove the serum-free medium and the formulation, and cultured in a medium containing 10% calf serum. The cells were observed by fluorescence microscopy with time course to check the EGFP expression. As a control, a PBS solution containing an equal amount of pCMV-EGFP, and a complex of a cationic liposome formulation and pCMV-EGFP were each added to the 293 cells.

Figure 6:
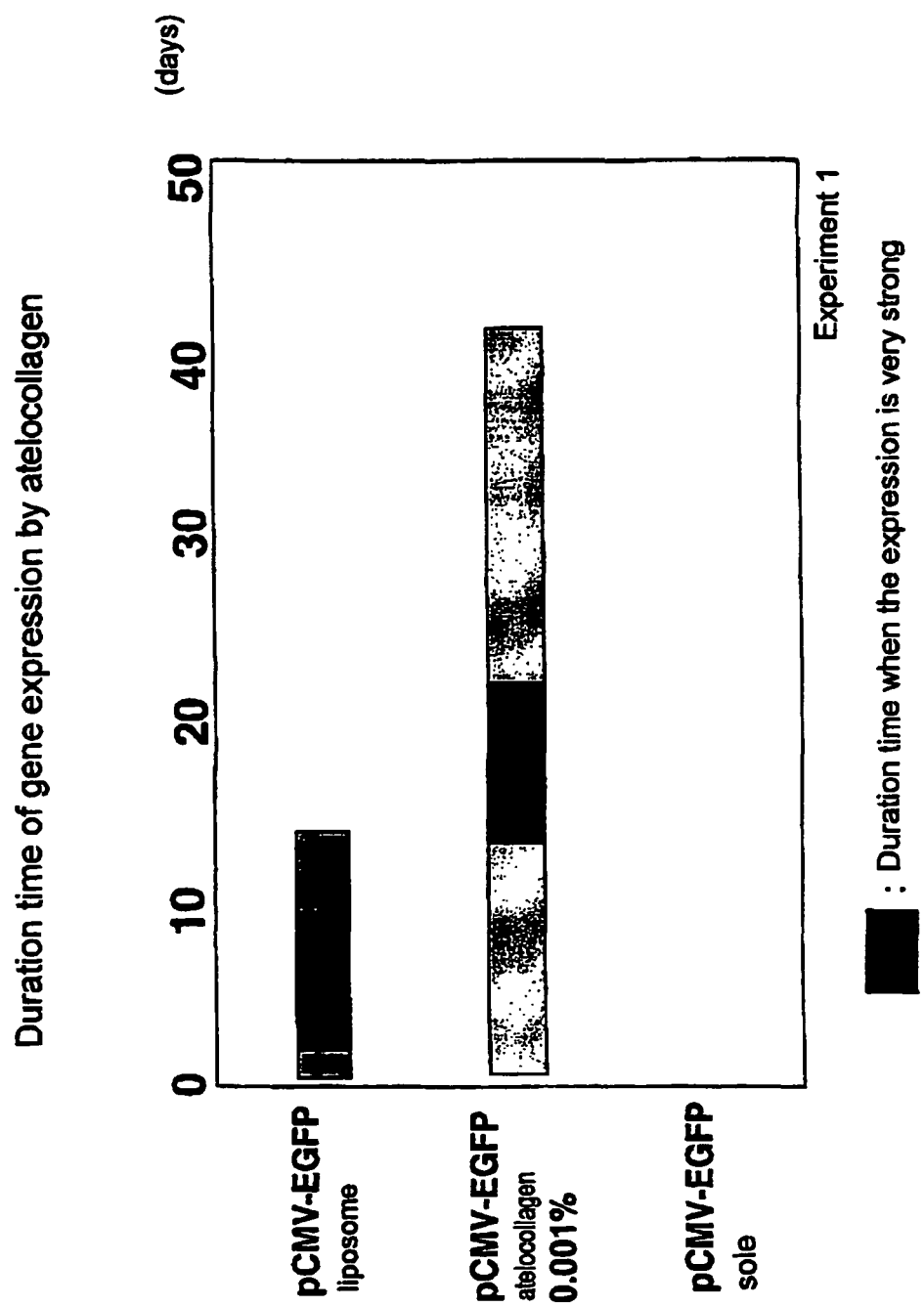
FIG. 6 is a graph showing a comparison in the duration time of gene expression among the atelocollagen gel formulation, the cationic liposome formulation, and the plasmid DNA in a PBS solution.

The results are shown in FIG. 6. In case of the gel formation of pCMV-EGFP, the expression of EGFP was observed, and the expression was found to maintain during a long period of time up to 52 days after the addition. On the other hand, in case of the PBS solution containing pCMV-EGFP, no expression of EGFP was observed, and in case of the cationic liposome formulation, the expression of EGFP was found to merely maintain during a short period of time for 2 days. These results shows that the formulation of a plasmid DNA with a collagen promotes the expression efficiency of a plasmid DNA, and maintains the expression during a longer period of time.

This means that a complex as formed with a plasmid DNA and a collagen promotes the transfer of a plasmid DNA into a cell, and enhances the stability of the plasmid DNA inside and outside the cell, resulting in extension of the gene expression in the cell. Without being limited to a particular theory of operation, it is believed that the fact that the expression was extended for a longer period of time in the absence of any complex in the system shows that the complexes interact with the cells as strongly as that the complexes are not removed by the washing, or that the complexes are incorporated into the cells.

Example 4

Effect of the Composition of Complexes on Transfer Efficiency of Plasmid DNAs

Using pCMV-EGFP as a plasmid DNA, complexes having the composition as shown in Table 1 were prepared.

TABLE 1

| complex | atelocollagen (%) | pDNA (μg/ml) |
|---------|-------------------|--------------|
| EGFG-1  | 0                 | 100          |
| EGFG-2  | 0.001             | 100          |
| EGFG-3  | 0.01              | 100          |
| EGFG-4  | 0.05              | 100          |
| EGFG-5  | 0.1               | 100          |

The results show that their transfer efficiencies are promoted in order of EGFG-3 complex>EGFG-2 complex>EGFG-4 complex=EGFG-5 complex. No transfer was found in EGFG-1. This shows that the formation of a plasmid DNA with a atelocollagen promotes the expression efficiency of a plasmid DNA, and that the expression efficiency in the complexes containing the equal amount of plasmid DNA varies depending on the content of atelocollagen.

Example 5

Effects of the Amounts of Plasmid DNA on the Transfer Efficiency of DNA Plasmid

Zero, 10, 50, 100, 250, and 500 μl of EGFG-3 complex (0.01% atelocollagen, 100 μg/ml pCMV-EGFP), which was found in Example 4 that the transfer efficiency is the highest, was added to the 293 cells cultured on a 6-well dish in the presence of 1 ml of serum-free medium. Then, after cultured at 37° C. overnight, the cells were washed with PBS to remove the serum-free medium and the complex, and the medium was replaced for a 10% FBS (a medium containing 10% calf serum). The cells were observed by fluorescence microscopy with time course over 6 days to check the EGFP expression.

When the amount of plasmid DNA is increased, then the transfer efficiency was also improved. Particular data are shown in the followings. In the table, expression efficiency was estimated by counting the number of the cells emitting fluorescence caused by EGFP expression among the counted number of all cells existing in the compartment defined by the microscopic range.

TABLE 2

| | Transfection efficiency | | |
|---|---|---|---|
| EGFG-3 (μl) | 100 | 250 | 500 |
| EGFP expressing cells (cells/wel) | 262 | 1057 | 1081 |
| efficiency | 0.006 | 0.03 | 0.03 |

Example 6

Comparison in Extension Effects of Complexes on Duration Time of Expression Between the Dropwise Addition and Solid Coating of the Complexes First, the composition of a collagen and a plasmid DNA was optimized on the basis of the composition of EGFG-3 complex (0.01% atelocollagen, 100 μg/ml pCMV-EGFP), which was found that the transfer efficiency is the highest, and then, the duration times of expression were compared between the dropwise addition and the solid coating.

(1) Using pCMV-EGFP as a plasmid DNA, complexes having the various compositions of atelocollagen concentrations as shown in Table 3 were prepared.

TABLE 3

Experiment 6: Gene-transfection efficiency relative to atelocollagen

| complex | atelocollagen (%) | pDNA (μg/ml) |
|---|---|---|
| EGFG-3A | 0.005 | 100 |
| EGFG-3B | 0.008 | 100 |
| EGFG-3 | 0.01 | 100 |
| EGFG-3C | 0.015 | 100 |
| EGFG-3D | 0.02 | 100 |
| EGFG-3E | 0.03 | 100 |
| pDNA solely | 0 | 100 |

Figure 7:
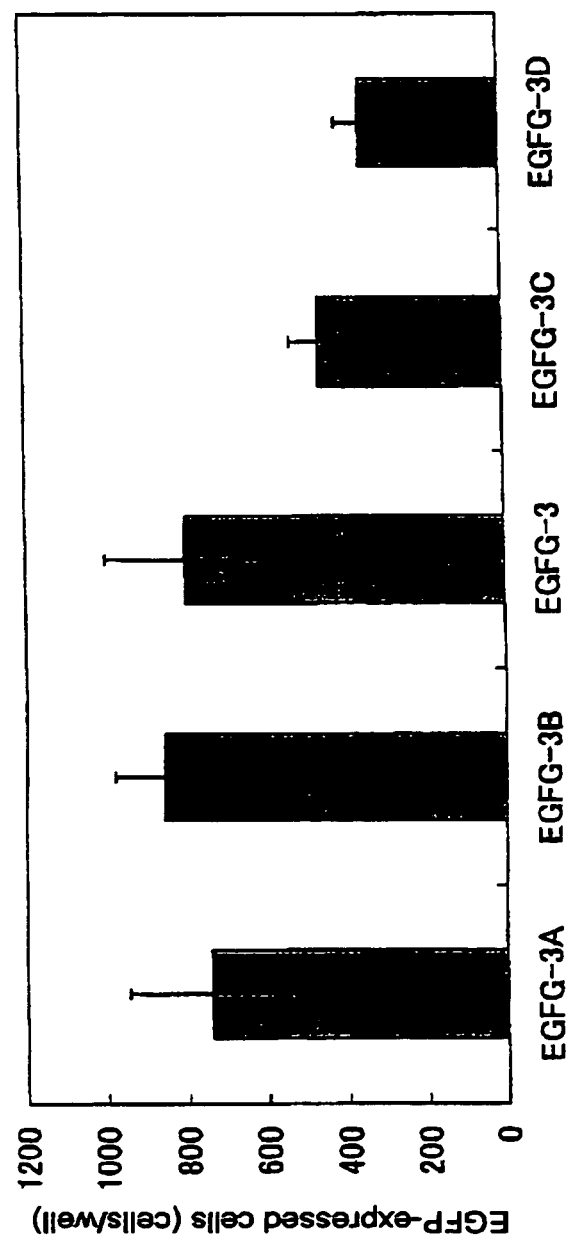
FIG. 7 is a graph showing the relationship between the complexes comprising a collagen in various concentrations and the transfer efficiency of plasmid DNA seven days after the transfection by dropwise addition.
Figure 8:
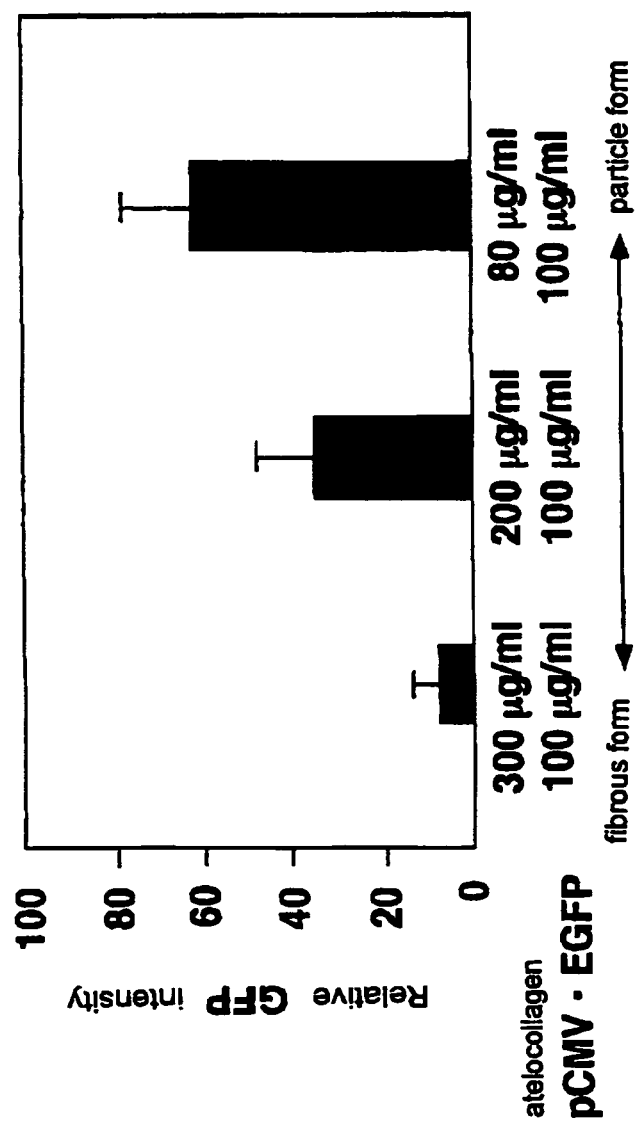
FIG. 8 is a graph showing a fluorescence intensity representing the transfer efficiency of plasmid DNA in the complexes comprising a collagen in various concentrations seven days after the transfection.

The complexes prepared were added dropwise to the 293 cells cultured on a 6-well dish in the presence of serum-free medium. Then, after cultured at 37° C. overnight, the cells were washed with PBS to remove the serum-free medium and the complex, and the medium was replaced for a medium containing 10% calf serum. Seven days later, the cells were observed by fluorescence microscopy, and the cells expressing EGFP were counted. The results are shown in FIG. 7. For EGFG-3B, 3D, and 3E, fluorescence intensities of the expressed EGFP were measured (Array Scan II System, Cellomics, Co.). Relative fluorescence intensities are shown in FIG. 8.

The complexes prepared were coated onto a 6-well dish at 250 μl/well, and the dish was air-dried for 30 minutes. Then, the 293 cells ($4-5 \times 10^5$ cells/well) in a medium containing 10% FBS were added thereto, and cultured at 37° C. overnight. Seven days later, the cells were observed by fluorescence microscopy, and the cells expressing EGFP were counted. The results are shown in FIG. 9.

Figure 9:
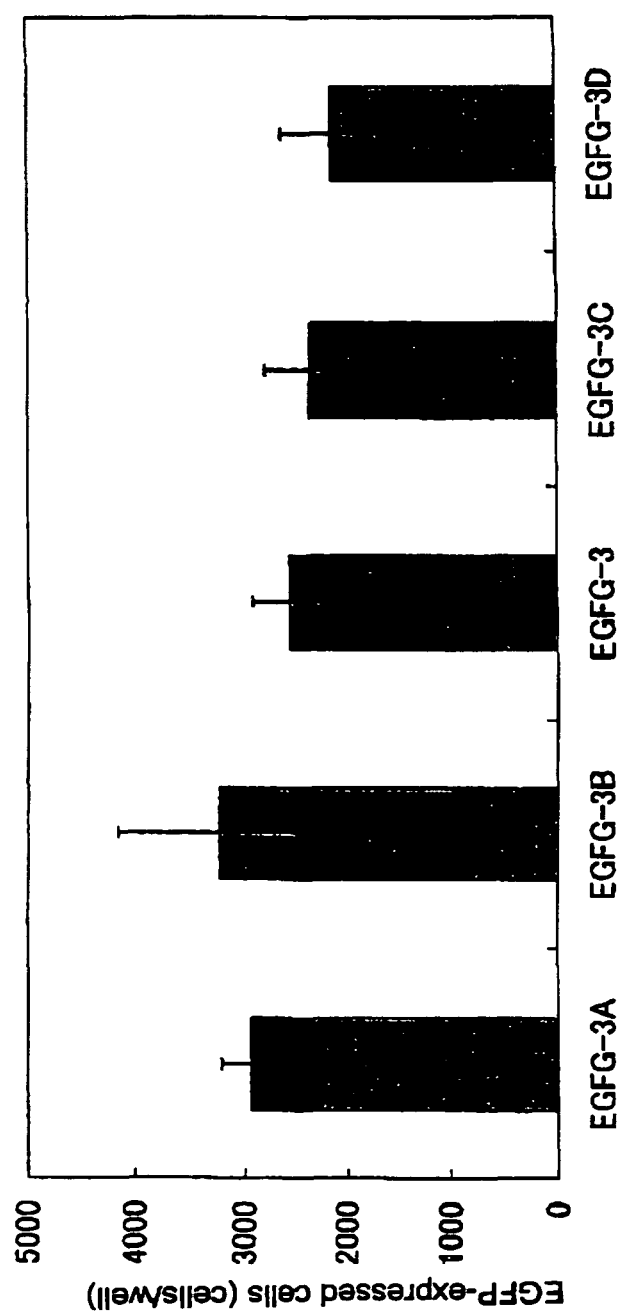
FIG. 9 is a graph showing the relationship between the complexes comprising a collagen in various concentrations and the transfer efficiency of plasmid DNA seven days after the transfection by solid coating.

FIG. 7 showing the results of dropwise addition and FIG. 9 showing the results of solid coating indicate that the concentration of collagen affects the transfer efficiency, and the solid coating is superior to the dropwise addition in transfer efficiency.

(2) Complexes having the various compositions of plasmid DNA concentrations as shown in Table 4 were prepared, and transfer efficiencies were compared between dropwise addition and solid coating.

TABLE 4

| complex | atelocollagen (%) | pDNA (μg/ml) |
|---|---|---|
| EGFG-3B | 0.008 | 100 |
| EGFG-3B2 | 0.008 | 60 |
| EGFG-3B3 | 0.008 | 40 |
| EGFG-3B4 | 0.008 | 20 |

Figure 10:
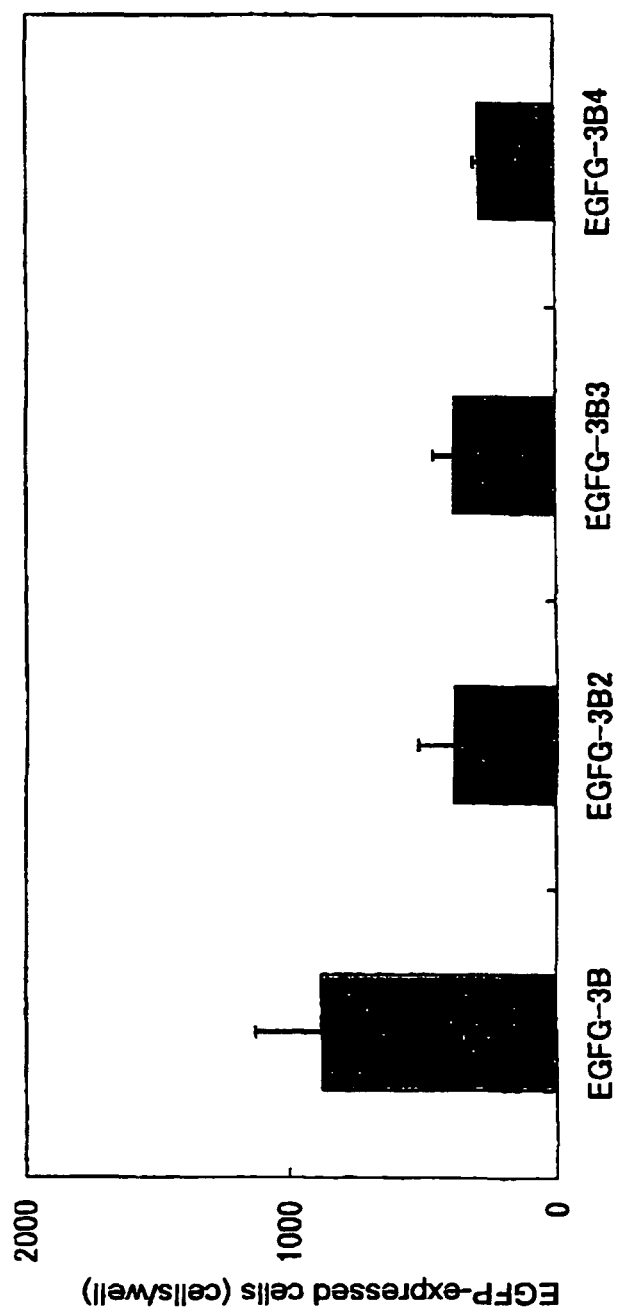
FIG. 10 is a graph showing the relationship between the complexes comprising a plasmid DNA in various concentrations and the transfer efficiency of plasmid DNA seven days after the transfection by dropwise addition.
Figure 11:
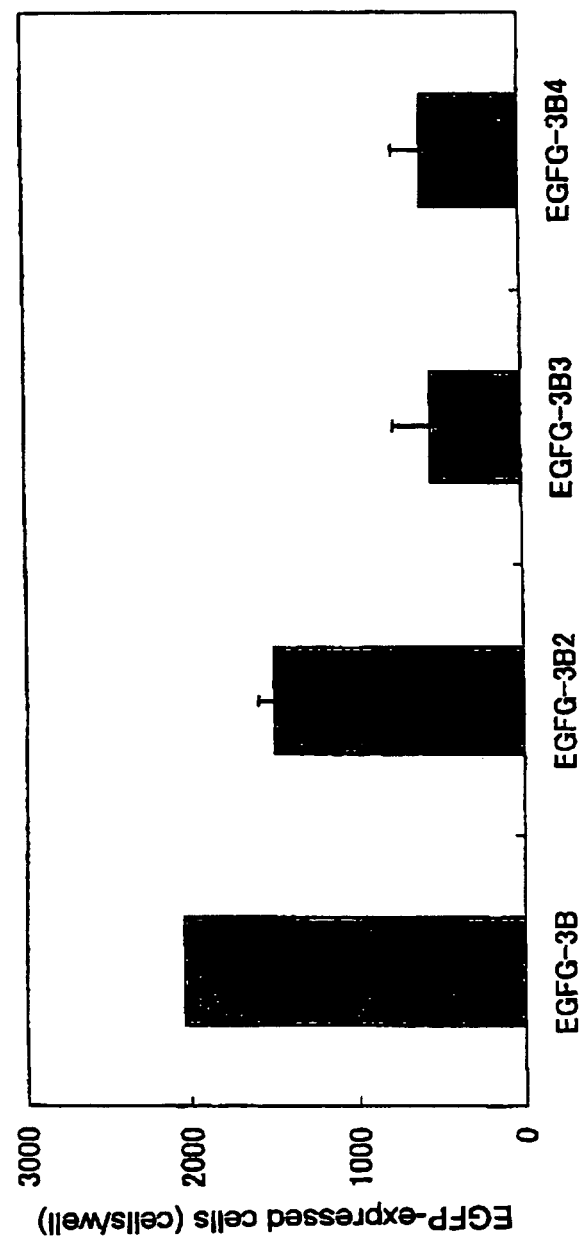
FIG. 11 is a graph showing the relationship between the complexes comprising a plasmid DNA in various concentrations and the transfer efficiency of plasmid DNA seven days after the transfection by solid coating.
Figure 12:
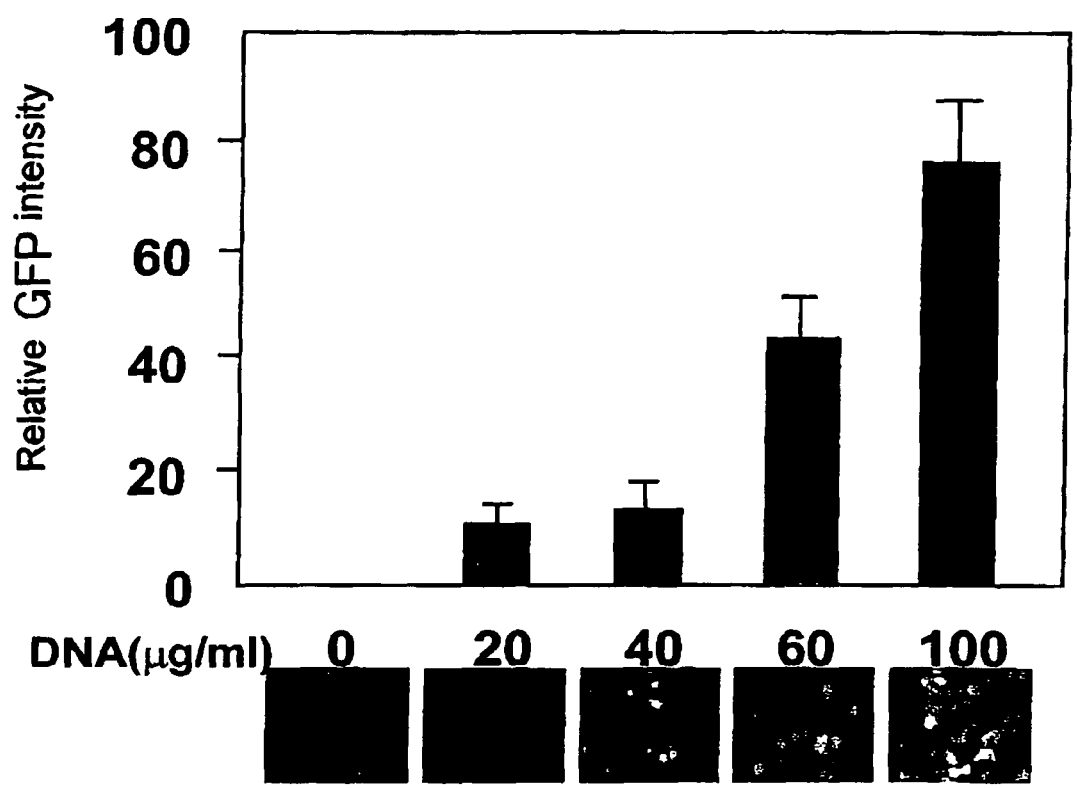
FIG. 12 is a graph showing a fluorescence intensity representing the transfer efficiency of plasmid DNA seven days after the transfection by dropwise addition, and a micrograph showing the fluorescence.

The results of dropwise addition are shown in FIG. 10, and the results of solid coating are shown in FIG. 11. Relative fluorescence intensities of EGFP in each sample obtained in solid coating are also shown in FIG. 12. These results show that the concentration of plasmid DNA affects the transfer efficiency, specifically the expression level of EGFP and the concentration of plasmid or DNA are in a positive correlation, and also that the solid coating is superior to the dropwise addition in transfer efficiency.

Example 7

Application of Solid Coating to Screening Method

Ten μM of a phosphorothioate antisense oligonucleotide (5'-CTCGTAGGCGTTGTAGTTGT-3'; Molecular weight, about 6500; SEQ ID NO: 2) (5) (Sawaday) having a sequence complementary to a sequence from 4196 bp to 4216 bp of fibroblast growth factor HST-1 (FGF4) gene (described in Proc. Natl. Acad. Sci. USA, 84, 2890-2984 (1987)) was mixted with a 0.05% solution of atelocollagen to form complexes. The complexes were coated onto the bottom of a 96-well plate for cell culture, and air-dried to obtain a cell culture instrument wherein the bottoms were coated with the complex. Similarly, a phosphorothioate sense oligonucleotide (5'-GAGCATCCGCAACATCAACA-3'; SEQ ID NO: 3) (1) having the same sequence as the HST-1 gene, as well as phosphorothioate antisense oligonucleotides having a sequence (5'-AGTCGCATGCACACAACACA-3'; SEQ ID NO: 4) (2) as obtained by scrambling the antisense oligonucleotide sequence, and the three random sequences (5'-GACCATCGTCGATTCCAGT-3'; SEQ ID NO: 5) (3), (5'-CATGAACATCCTGAGCATCC-3'; SEQ ID NO: 6) (4), and (5'-GTTCACGAAGAAAGAAGGCT-3'; SEQ ID NO: 7) (6)) were each complexed with a collagen to form complexes, which complexes were coated onto the bottom, and dried. Onto the plate coated with those oligonucleotides, NEC8 cells in which the proliferation was promoted by overexpression of HST-1, and HepG2 cells in which the proliferation was promoted by the gene other than HST-1 were seeded at $0.5 \times 10^5$ cells/well, and the cells were cultured for 4 days. After the culture, the inhibition of cell proliferation was assayed using TetraColor ONE Cell Proliferation Assay Reagent. Specifically, the sample solution stained was determined spectrometrically at 650 nm, using the absorbance at 450 nm as control (FIG. 13).

Figure 13:
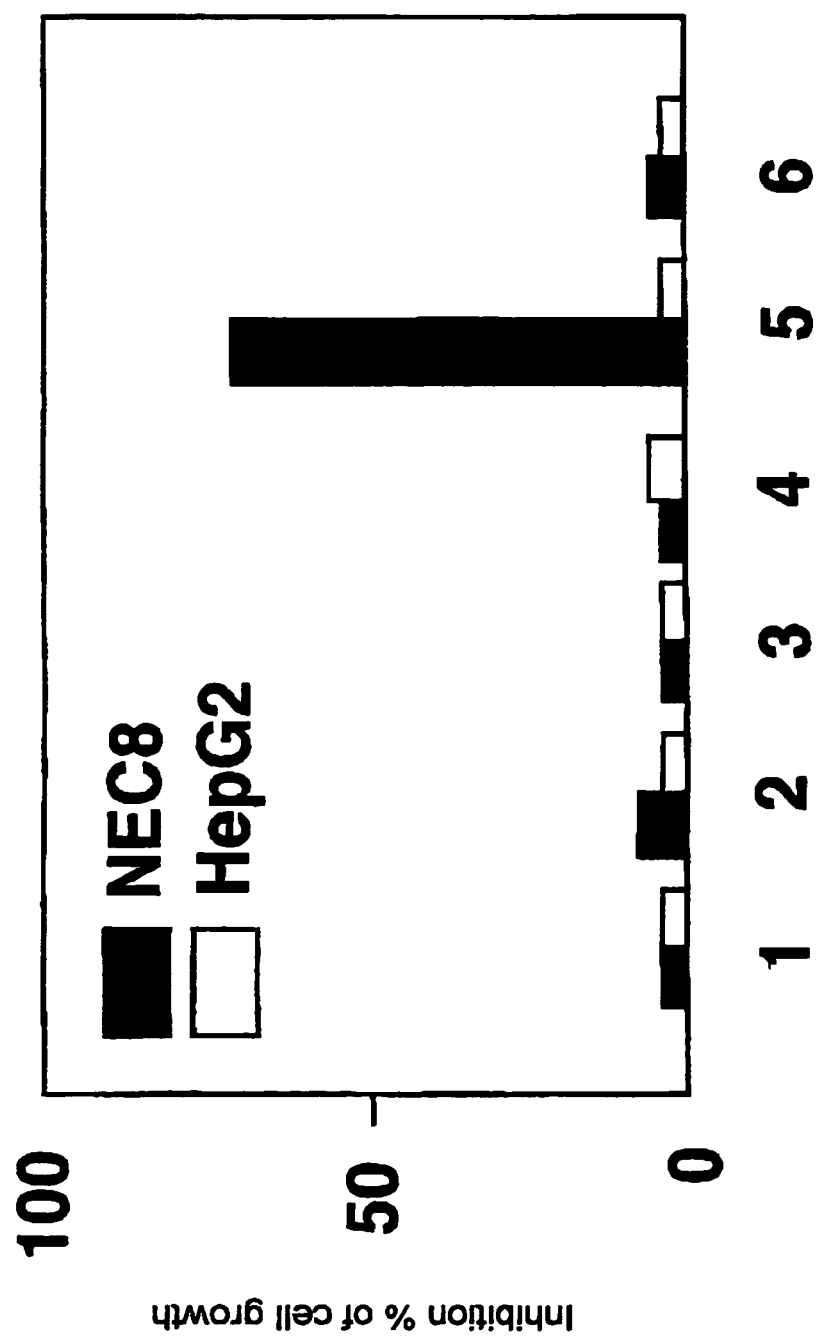
FIG. 13 is a graph showing inhibitory effects of the present invention on the cell proliferation.

As a result, the inhibitory effect of NEC 8 cells proliferation was observed only in the case of coating of the complex formed between an antisense oligonucleotide against HST-1 and a collagen (FIG. 13-5). On the other hand, no inhibitory effect was observed in the case of coating of the complex formed between a sense oligonucleotide against HST-1 and a collagen onto the bottom of the plate (FIG. 13-1). Also, no inhibitory effect was observed in the case of coating of the complex formed between the phosphorothioate antisense oligonucleotides having the sequence as scrambling the antisense oligonucleotide sequence (FIG. 13-2) and the random sequences (FIG. 13-3, 4, 6) and a collagen onto the bottom of the plate. These results show that it is possible to screen for a gene responsible for the cell proliferation without reagents for gene transfer such as cationic liposomes and cationic lipids, which do not usually exist in living bodies, when an antisense oligonucleotide complexed with an atelocollagen is coated onto the solid phase, and cells are cultured thereon. Further, these results show that the present process enables to examine sensitively the gene functions even using a small amount of the cells and the oligonucleotides without noise due to damage to cells from gene transfer reagents.

Example 8

Storage of Adenovirus Vector Under Air Drying Using Atelocollagen

Preparation by Solid Coating

Ten μl of a solution of an adenovirus vector, AdCMVEGFP (K. Aoki, et al., Mol. Ther. (2000) 1 (6): 555-565) at $1 \times 10^8$ pfu/ml in a DMEM solution was mixed with 5 μl of a 2% solution of an atelocollagen in PBS (−). Fifty μl of the mixture was added to a 24-well culture plate (non-coated) (Corning Inc.), and the plate was air-dried with a dryer set on the cool mood at room temperature for 15 minutes to carry out the solid coating.

Test of Viruses for Stability During Storage

While the resultant culture plate was left at it was at room temperature, a human hepatoma cell line, the HepG2 cells were added thereto at 2×10⁵ cells/well 1 day, 7 days and 14 days after the leaving, and each 2 days later, the expression level of GFP was observed by fluorescence microscopy. As control, a similar experiment was carried out using a culture plate coated with only adenovirus, and with only an atelocollagen.

The results are shown in Table 5.

TABLE 5

| | | GFP-positive cells ratio 2 days after the seeding (%) | |
|---|---|---|---|
| | | atelo/adeno | only adeno | only atelo |
| left at r.t. | 1 day | 64 | 72 | 0 |
| left at r.t. | 7 days | 42 | 10 or less | 0 |
| left at r.t. | 14 days | | | | r.t. means room temperature.

Table 5 shows that the adenovirus vector survived during storage for even 14 days, suggesting that the solid coating of the present invention provides a plate for screening that comprises adenovirus vectors, which could be conveniently distributed on the market.

Example 9

Figure 14:
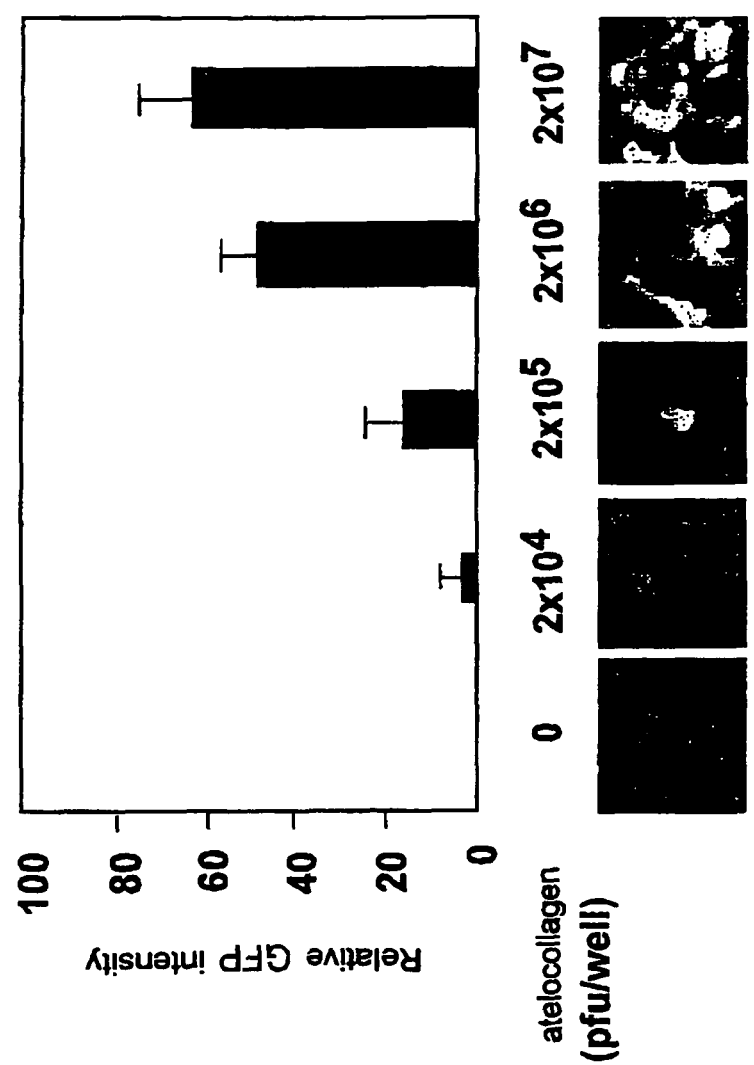
FIG. 14 is a graph showing that adenovirus was transferred by solid coating in a dose-dependent manner, and a micrograph showing the fluorescence.

Gene Transfer Effects of the Solid Coating in a Dose-Dependent Manner of Adenovirus Both equal amounts of a solution of an adenovirus vector AdCMVEGFP (K. Aoki, et al. Mol. Ther. (2000) 1 (6): 555-565) in DMEM at 4×10⁴, 4×10⁵, 4×10⁶ and 4×10⁷ pfu/ml, and a 160 μg/ml solution of an atelocollagen were mixed together. The mixture could be stored at 4° C. for a long period of time without lowered activity. Fifty μl of the mixture was added to a 96-well culture plate (non-coated; Corning Inc.), and the plate was air-dried to carry out the solid coating. The plate can be stored at least for 2 weeks to 4 weeks without lowered activity. Embryonic stem cells (ES cells) were seeded on the resultant culture plate, and three days later, the expression of GFP was checked with fluorescence microscopy, simultaneously with determining the fluorescence intensity. As a result, it was found that the fluorescence intensity of GFP is positively correlated with the dose of adenovirus (FIG. 14). The results shows that the present invention should provide a useful tool for high-throughput screening for ES cells using adenovirus, and a plate for screening, which is coated with complexes formed by adenovirus and collagen.

Example 10

Relationship Between the Composition of Complexes Comprising Plasmid DNAs and the Average Major Axis Both equal amounts of an aqueous solution, a 0.1 M phosphate buffer (PB) or a 0.01 M phosphate buffer (PBS) containing sodium chloride, each of which contained a plasmid DNA encoding a fluorescent protein (EGFP) (pCMV-EGFP/pEGFP—N1, 4.7 kbp, Clontech Co.) at 200 μg/ml and was cooled up to 10° C. or less, and an aqueous solution containing an atelocollagen (KOKEN CO., LTD.) at 0.002 to 0.02% (w/w) cooled up to 10° C. or less were mixed together, and the mixtures were left as they were overnight at 10° C. or less so as to prepare a formulation in a gel form. The gel formulation was penetrated through a filter having a pore size of 70 μm or 10 μm to prepare a gel formulation having an ordered size.

To the formulation, PicoGreen dsDNA Quantitation Reagent (Molecular Probes) was added to stain pCMV-EGFP, and the major axis of the complexes were determined by fluorescent microscopy. Similarly, a plasmid DNA (pCMV-HST-1-IL-2, 6.2 kbp) encoding the secretory signal peptide of HST-1 and interleukin-2, and an atelocollagen were mixed together to prepare a formulation in a gel form, and the major axis of the complexes was determined. Further, the gel formulation was electrophoresed on agarose gel (Tris-acetate buffer, 0.8% agarose gel) to separate plasmid DNAs formed into complexes from those not formed into complexes. The band of the plasmid DNAs that were not formed into complexes was stained with ethidium bromide, and the fluorescence intensity was determined with Fluor-S-Multi Imager (BIO-RAD). Amount of the plasmid DNAs that were not formed into complexes were determined on the basis of the standard curve obtained from the fluorescence intensity of the band of the plasmid DNA with the known concentration as electrophoresed, and the ratio of the negative charge of the DNA contained in the complex to the molecular weight of the collagen. The results are shown in Table 6.

TABLE 6

| | | | | | Average major axis of complexes (μm) | | |
|---|---|---|---|---|---|---|---|
| Sample | Plasmid DNA | Solv. | C.C. (%) | Number of N.M per C.M | After mixing | After 70 μm filter | After 10 μm filter |
| 10-1 | pCMV-EGFP | Water | 0.001 | 2406 | 9.1 | 8.9 | <3.4 |
| 10-2 | pCMV-EGFP | Water | 0.005 | 742 | 37 | 26 | |
| 10-3 | pCMV-EGFP | Water | 0.008 | 699 | 6.6 | | |
| 10-4 | pCMV-EGFP | Water | 0.01 | 299 | 53 | 44 | 35 |
| 10-5 | pCMV-EGFP | Water | 0.02 | 356 | 17 | | |
| 10-6 | pCMV-EGFP | Water | 0.05 | 76 | 122 | 105 | |
| 10-7 | pCMV-EGFP | Water | 0.1 | 66 | 303 | 174 | |
| 10-8 | pCMV-EGFP | PB | 0.001 | 448 | <3.4 | | <3.4 |
| 10-9 | pCMV-EGFP | PB | 0.01 | 152 | 7.7 | | |
| 10-10 | pCMV-EGFP | PB | 0.1 | 97 | 22 | | 14 |
| 10-11 | pCMV-EGFP | PBS | 0.01 | 300 | 13 | | 9.2 |
| 10-12 | pCMV-EGFP | PBS | 0.1 | 97 | 22 | | 15 |
| 10-13 | pCMV-HST-1-IL-2 | Water | 0.001 | 4228 | 6 | 6.1 | <3.4 |

TABLE 6-continued

| Sample | Plasmid DNA | Solv. | C.C. (%) | Number of N.M per C.M | Average major axis of complexes (μm) | | |
|---|---|---|---|---|---|---|---|
| | | | | | After mixing | After 70 μm filter | After 10 μm filter |
| 10-14 | pCMV-HST-1-IL-2 | Water | 0.005 | 1122 | 20 | 9.8 | |
| 10-15 | pCMV-HST-1-IL-2 | Water | 0.008 | 426 | 6.1 | | |
| 10-16 | pCMV-HST-1-IL-2 | Water | 0.01 | 324 | 20 | 13 | 27 |
| 10-17 | pCMV-HST-1-IL-2 | Water | 0.02 | 360 | 16 | | |
| 10-18 | pCMV-HST-1-IL-2 | Water | 0.05 | 95 | 151 | 201 | |
| 10-19 | pCMV-HST-1-IL-2 | Water | 0.1 | 66 | 256 | 201 | |
| 10-20 | pCMV-HST-1-IL-2 | PB | 0.001 | 701 | 6.1 | | <3.4 |
| 10-21 | pCMV-HST-1-IL-2 | PB | 0.01 | 262 | 20 | | |
| 10-22 | pCMV-HST-1-IL-2 | PB | 0.1 | 97 | 25 | | 9.4 |
| 10-23 | pCMV-HST-1-IL-2 | PBS | 0.01 | 315 | 9.8 | | |
| 10-24 | pCMV-HST-1-IL-2 | PBS | 0.1 | 97 | 29 | | |

In the table, "Solv." means solvent. "C.C. (%)" means collagen concentration (%). "Number of N.M per C.M" means number of nucleotide monomer per collagen molecule. "After 70 μm filter" means after penetrating through a filter having a pore size of 70 μm. "After 10 μm filter" means after penetrating through a filter having a pore size of 10 μm.

In both cases of pCMV-EGFP and pCMV-HST-1-IL-2, a water without salts was used as a solvent to obtain complexes wherein the average major axis is 122 μm or more, when collagen concentration was 0.05% or more. When collagen concentration was 0.005% to 0.02%, complexes having an average major axis of 6.1 μm to 53 μm were obtained, and when collagen concentration was 0.001%, complexes having an average major axis of 10 μm or less were obtained. The results show that the form or the shape of a complex can be controlled by adjusting the concentration of a plasmid DNA and a collagen to be mixed, when a water without salts is used as a solvent.

The results are consistent with those as obtained in Example 2 wherein pCAHST-1 was used to prepare complexes. The plasmid DNAs as used therein were different each other in size as pCAHST-1 is 7.9 kbp, pCMV-EGFP is 4.7 kbp, and pCMV-HST-1-IL-2 is 6.2 kbp, showing that sizes of plasmid DNAs never affect the form or the shape of complexes to be formed.

On the other hand, 0.1 M phosphate buffer and 0.01 M phosphate buffer containing sodium chloride were used as a solvent to obtain complexes having an average major axis of 3.4 μm to 29 μm, and no complexes having a 100 μm or more in size, when collagen concentration was 0.001% to 0.1%. It was believed that this was caused by the salts, which inhibited the formation of collagen association bodies, showing that when complexes are prepared in the presence of an agent that inhibits the formation of collagen association body, then complexes having an average major axis of 100 μm or less can be prepared irrespective of collagen concentration.

Further, when the gel formulation as obtained by mixing a plasmid DNA and a collagen was penetrated through a filter having a pore size of 70 μm or 10 μm, complexes having a smaller average major axis and having an ordered size could be prepared.

Figure 15:
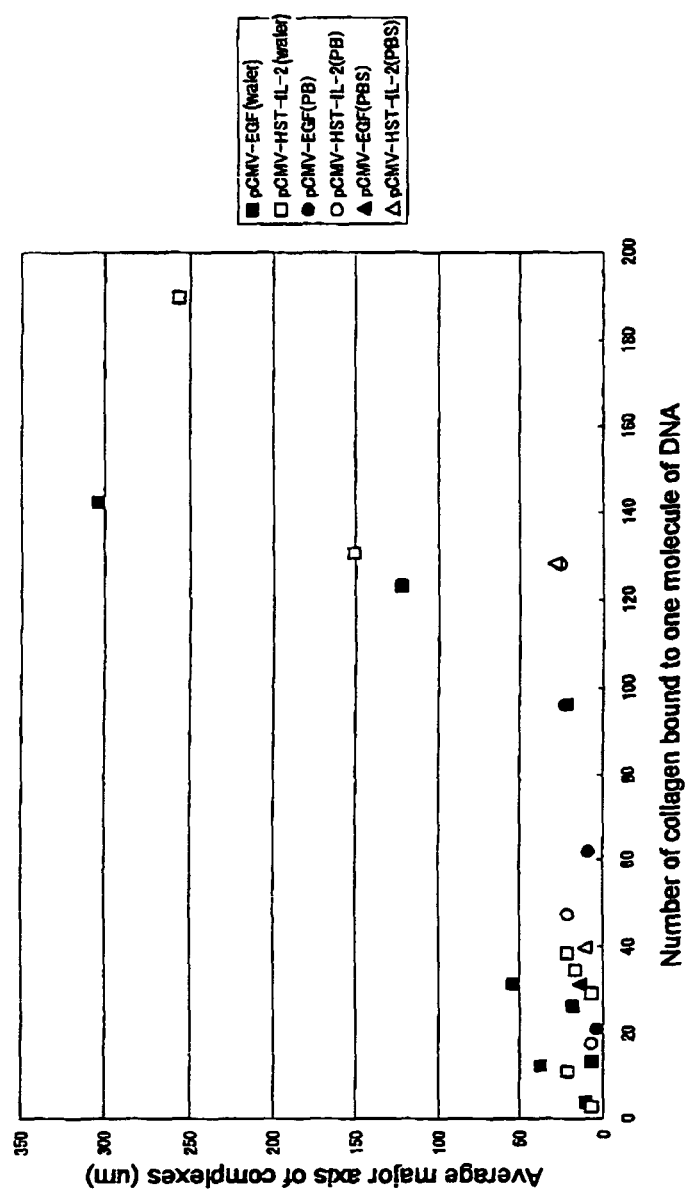
FIG. 15 is a graph showing the relationship between the number of collagen bound to one molecule of plasmid DNA and the average major axis of the complexes.

FIG. 15 shows the relationship between the number of collagen bound to one molecule of plasmid DNA and the average major axis of the complexes. In both cases of pCMV-EGFP and pCMV-HST-1-IL-2 as used in a water without salts, it was found that the average major axis of complexes trends to extend as increasing in the number of collagen bound to plasmid DNA. On the other hand, when 0.1 M phosphate buffer and 0.01 M phosphate buffer containing sodium chloride were used as a solvent to prepare complexes, such trend as above was not found, and even in the condition that collagen molecules having an average major axis of 100 μm or more was complexed with a plasmid DNA in case of the use of a water as a solvent, the average major axis did not exceed 50 μm. It is understood that this is caused by extension reaction along the major axis of collagen association body, of which formation is developed by the formation of complexes of a plasmid DNA and a collagen as observed in the case that a water is a solvent as mentioned above. On the other hand, in case of the presence of salts, it is understood that collagen association body formed by attaching a collagen molecule with a plasmid DNA does not extend along the major axis well, and therefore a lot of fine association bodies attach to a plasmid DNA to form a structure. Collagens have been known to form fine association bodies at appropriate salt concentrations. Thus, it can be considered that a partial amount of collagens has already formed with a plasmid DNA into fine bodies before mixing with a plasmid DNA, and the fine collagen association bodies are attached to a plasmid DNA to form complexes. This means that complexes having an average major axis of 50 μm or less can be prepared by mixing a plasmid DNA and a collagen that has been formed into fine association bodies.

Figure 16:
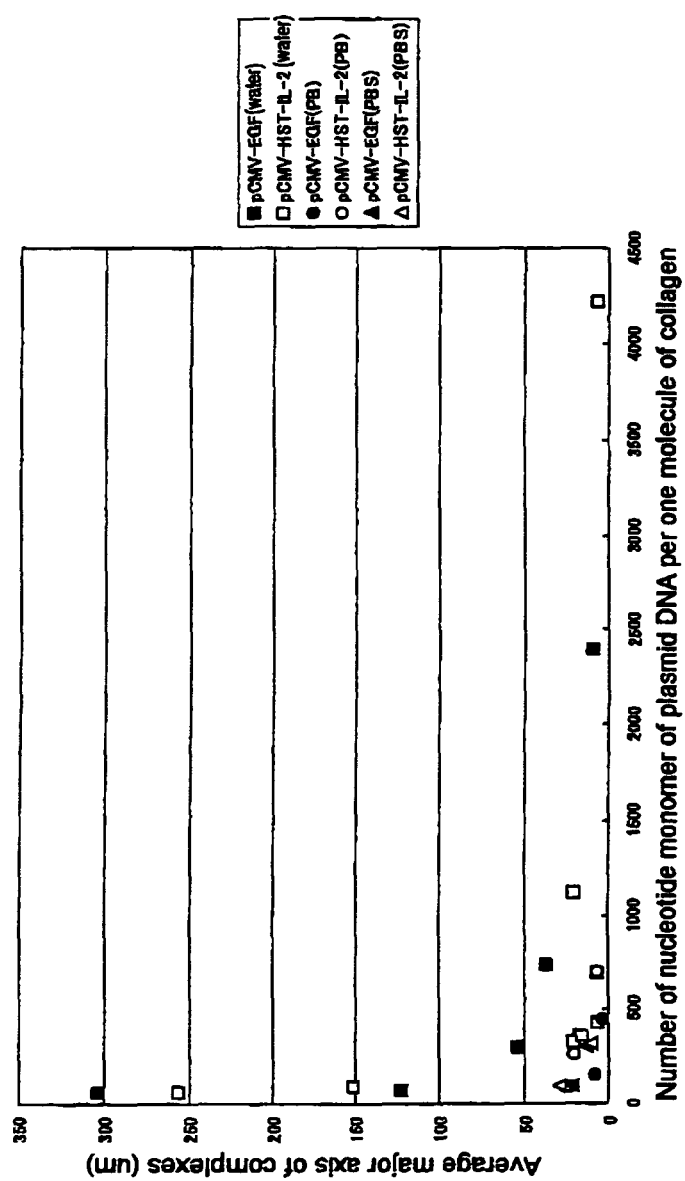
FIG. 16 is a graph showing the relationship between the number of nucleotide monomer of desired nucleic acids per collagen molecule and the average major axis of the complexes.

For the general analysis of those results regardless of size of plasmid DNAs, the number of nucleotide monomer of a plasmid DNA per one collagen molecule in complexes was counted. FIG. 16 shows the relationship between the number of nucleotide monomer of plasmid DNAs per one collagen molecule, and the average major axis of the complexes. It was found that the average major axis of complexes trends to extend as decreasing in the number of nucleotide monomer of plasmid DNAs.

Taken together FIG. 16 and Table 6, the followings are concluded. When the number of nucleotide monomer is 95 or less, the complexes having an average major axis of 120 μm or more were obtained. This means that the decrease in the number of nucleotide monomer per one collagen molecule represents the increase in the number of collagen molecules relative to the plasmid DNA in the complexes, and thus complexes having an average major axis of 120 μm or less can be prepared by keeping the number of nucleotide monomer of plasmid DNAs per one collagen molecule to be 96 or more. On the other hand, minimum unit of the complexes is a complex formed by one molecule of collagen and one molecule of plasmid DNA. One molecule of collagen and many plasmid DNA hardly form complexes since plasmid DNAs repel each other by their negative charge and undergo steric hindrance. Accordingly, the maximum number of nucleotide monomer per one collagen molecule is obtained by forming a complex with each one molecule of collagen and plasmid DNA, and is defined by the number of nucleotide monomer comprised in a plasmid DNA.

Example 11

Relationship Between the Composition and the Average Major Axis of the Complex Comprising an Oligonucleotide An equal amount of an aqueous solution, or a 0.1 M phosphate buffer (PB), each of which contained a phosphorothioate antisense oligonucleotide (5'-CTCGTAGGCGTTG-TAGTTGT-3'; Molecular weight, about 6500; SEQ ID NO: 8) (Espec Inc.) having a sequence complementary to a sequence from 4196 bp to 4216 bp of fibroblast growth factor HST-1 (FGF4) gene (described in Proc. Natl. Acad. Sci. USA, 84, 2890-2984 (1987)) in a concentration of 2.0 μM to 40.0 μM, and was cooled up to 10 CC or less, and an aqueous solution containing an atelocollagen (KOKEN CO., LTD.) at 0.002 to 3.0%(w/w) cooled up to 10° C. or less, 0.1 M phosphate buffer were each mixed together at 10° C. or less, and the mixtures were left as they were overnight at 10° C. or less so as to prepare formulations in a gel form. Oligonucleotide amounts that were complexed with a collagen in the gel formulations were determined as follows. The gel formulations were centrifuged at 150,000 rotations per hour at 5° C. to precipitate the complexes, and the amounts of the oligonucleotides released in the supernatant were determined by HPLC (column: Puresil C18 5 (Waters), mobile phase: a gradient of 24.5% to 35% acetonitrile over 35 minute in 0.1 M ammonium acetate containing 5 mM tetrabutyl ammonium and 1 mM EDTA, flow rate: 1 ml/min, detection wavelength: 260 nm). Single-Stranded nucleic acid fluorescence staining regent YOYO (Molecular Probes) was added to the resultant formulations to stain the oligonucleotides, which were observed by fluorescent microscopy to measure the major axis of the complexes. The results are shown in

TABLE 7

| Sample | Solv. | O.C.(μM) | C.C(%) | Number of O.M per C.M | Number of N.M per C.M | Average major axis of complexes (μm) |
|---|---|---|---|---|---|---|
| 11-1 | water | 1.0 | 0.05 | 0.6 | 12 | 32 |
| 11-2 | water | 5.0 | 0.05 | 3 | 60 | 13 |
| 11-3 | water | 10.0 | 0.05 | 4.4 | 88 | 12 |
| 11-4 | water | 20.0 | 0.05 | 5.2 | 104 | 17 |
| 11-5 | water | 10.0 | 0.01 | 6.3 | 126 | 32 |
| 11-6 | water | 10.0 | 0.1 | 2.9 | 58 | 20 |
| 11-7 | PB | 1.0 | 0.05 | 0.5 | 10 | 25 |
| 11-8 | PB | 5.0 | 0.05 | 1.2 | 24 | 29 |
| 11-9 | PB | 10.0 | 0.05 | 1.4 | 28 | 35 |
| 11-10 | PB | 20.0 | 0.05 | 1.3 | 26 | 36 |
| 11-11 | PB | 10.0 | 0.01 | 3.3 | 66 | 23 |
| 11-12 | PB | 10.0 | 0.1 | 1.3 | 26 | 33 |
| 11-13 | PB | 10.0 | 0.5 | 0.5 | 10 | 46 |
| 11-14 | PB | 10.0 | 1.0 | 0.3 | 6 | 49 |
| 11-15 | PB | 10.0 | 1.5 | 0.2 | 4 | 54 |

In the table, "Solv." means solvent. "O.C. (μM) means oligonucleotide concentration (μM)." "C.C. (%)" means collagen concentration (%). "Number of O.M per C.M" means number of oligonucleotide molecule per one collagen molecule. "Number of N.M per C.M" means number of nucleotide monomer per collagen molecule.

Similarly to Example 10 wherein plasmid DNAs were used, complexes were obtained by mixing oligonucleotides and collagens. In both cases of use of a water without salts and 0.1 M phosphate buffer as a solvent, there were no significant change in major axis of the complexes between the differences in the concentrations of collagen and oligonucleotide, which was different from the case of plasmid DNAs. This is believed to be caused by the fact that oligonucleotides are smaller than plasmid DNAs in molecular size, and thus the formation of collagen association bodies is inhibited.

Figure 17:
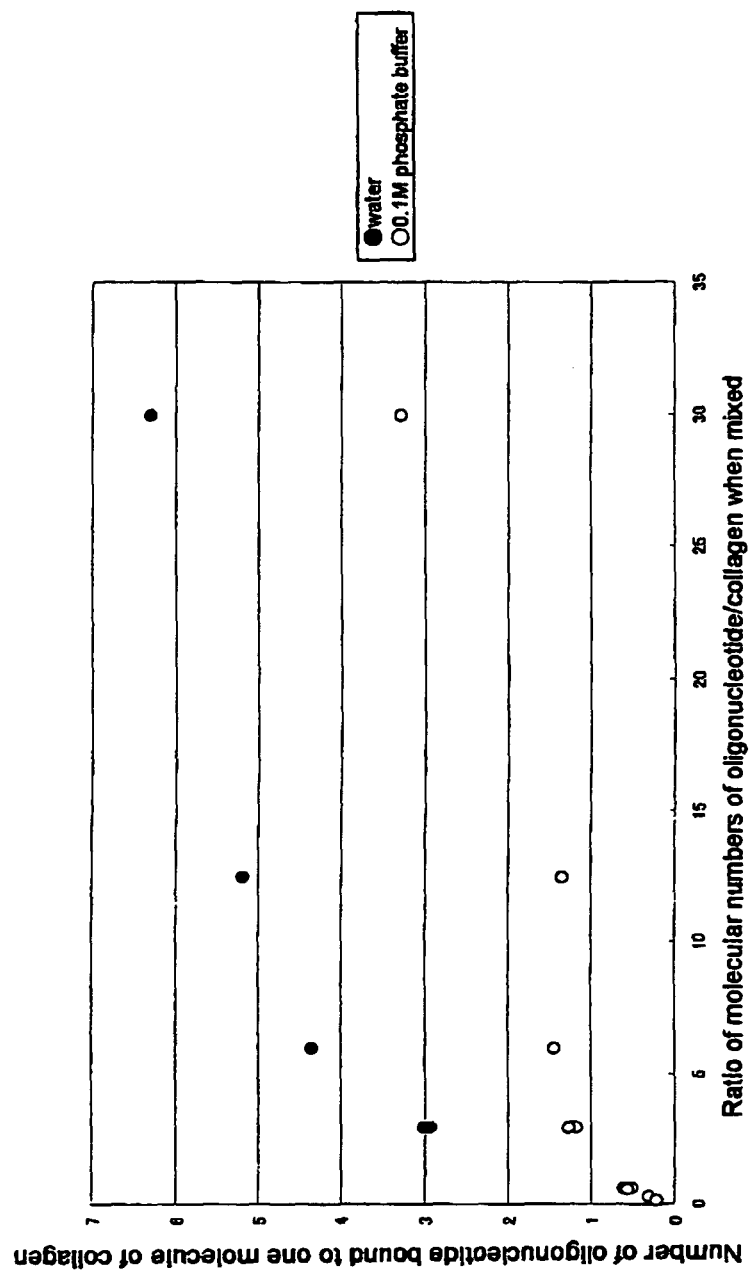
FIG. 17 is a graph showing the relationship between the molecular number ratio of oligonucleotide to collagen at the time of the mixture and the number of oligonucleotide bound to one molecule of collagen in the complex.

FIG. 17 shows the relationship between the molecular number ratio of oligonucleotide to collagen at the time of the mixture and the number of oligonucleotide bound to one molecule of collagen in the complex. It was found that the number of oligonucleotides bound to one collagen molecule in the formed complexes trends to increase as increasing in the number of oligonucleotides relative to the number of collagen molecule at the time of mixing in both cases that a water and the phosphate buffer were used as a solvent. The maximum number of oligonucleotide molecule bound to one collagen molecule varies depending on kinds of solvent, and it is 6 molecules in case of water, whereas it is 3 molecules in case of the phosphate buffer.

Since molecular weight of a collagen (300,000) is even larger than that of an oligonucleotide (about 6,500), and the form or the shape of complexes depends solely on the number of collagen molecule forming into complexes, the numbers of collagen molecule in complexes that have the same major axis are approximately the same. Accordingly, even for the complexes having the same major axis, the number of oligonucleotide molecule comprised in complexes varies depending on the number of oligonucleotide bound to one collagen molecule. Because individual complex contacts with a cell to allow oligonucleotides to be transferred into the cell, oligonucleotide transfer is more efficient when a complex that contains a high content of oligonucleotide molecules is used. Accordingly, a complex wherein the number of oligonucleotide molecule per one collagen molecule is increased is desired, and generally speaking, a complex wherein the number of nucleotide monomer bound to one collagen molecule is increased is preferred.

Example 12

Cell Culture Instrument Coated with a Complex Comprising an Oligonucleotide

Figure 18:
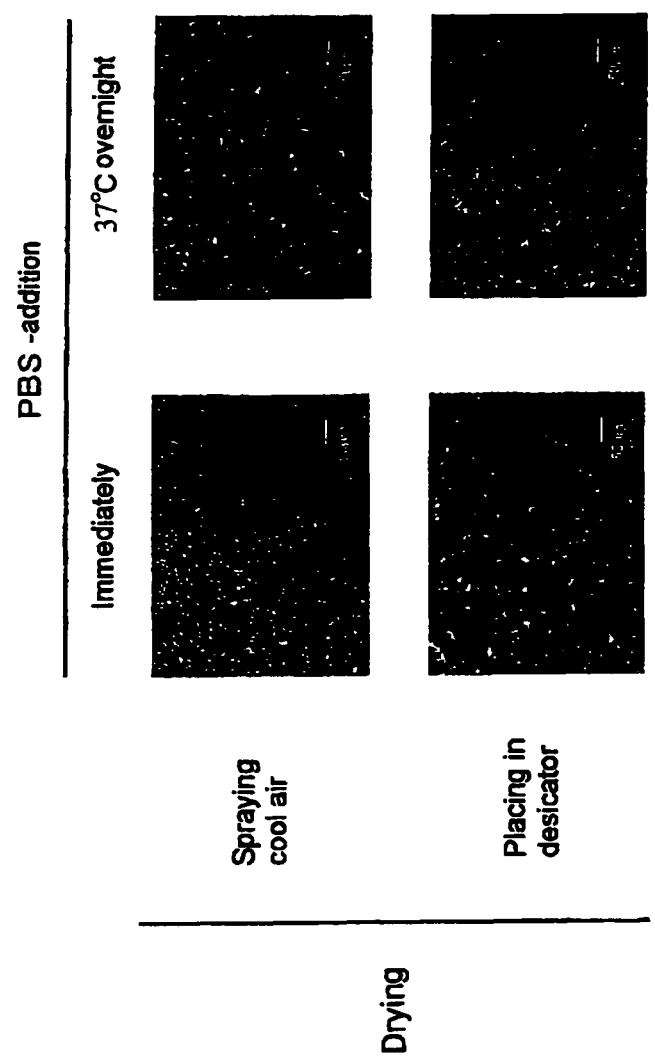
FIG. 18 is a fluorescence micrograph obtained by observing the complexes comprising the oligonucleotides released from the surface of the cell culture instrument according to the present invention with fluorescence microscopy.

Fifty μl of the gel formulation as prepared in Example 11 (11-3, the composition of the formulation of Example 7) was added dropwise to the bottom of a 96-well microplate, and dried by directly spraying a cool air (room temperature, 2 hours) or by placing in a desicator with silica gel (room temperature, 2 days) so as to prepare a cell culture instrument, of which the cell culture surface is coated with a complex. One hundred μl of 0.01 M phosphate buffer (PBS) that had been adjusted to be isotonic with living bodies by supplementing sodium chloride was added to the wells of the instrument, and the pipetting was slightly conducted immediately for sampling. Further, 100 μl of 0.01 M phosphate buffer (PBS) that had been adjusted to be isotonic with living bodies by supplementing sodium chloride was added to the wells of the instrument, and the instrument was left overnight at 37° C., followed by slightly pipetting for sampling. To 10 μl of the resultant sample, 2 μl of Single-Stranded nucleic acid fluorescence staining regent YOYO (Molecular Probes) was added to stain the oligonucleotides, and the complexes that released form the surface of the instrument were observed by fluorescent microscopy. The fluorescence micrograph is shown in FIG. 18. The complexes having a major axis of 50 μm or less were observed in all of the samples. This means that exposure on PBS allows to release complexes from the surface of a cell culture instrument. The form or the shape of the released complexes was not changed between before and after the coating onto the surface of the instrument irrespective of drying method, and condition of PBS exposure. This shows that the complexes are retained on the surface of a cell culture instrument with keeping their form or shape irrespective of drying method, and that the form or the shape of the complexes maintains in a temperature condition of 37° C. that is usually used in cell culture.

Example 13

Cell Culture Instrument Coated with a Complex Comprising a Plasmid DNA

Figure 19:
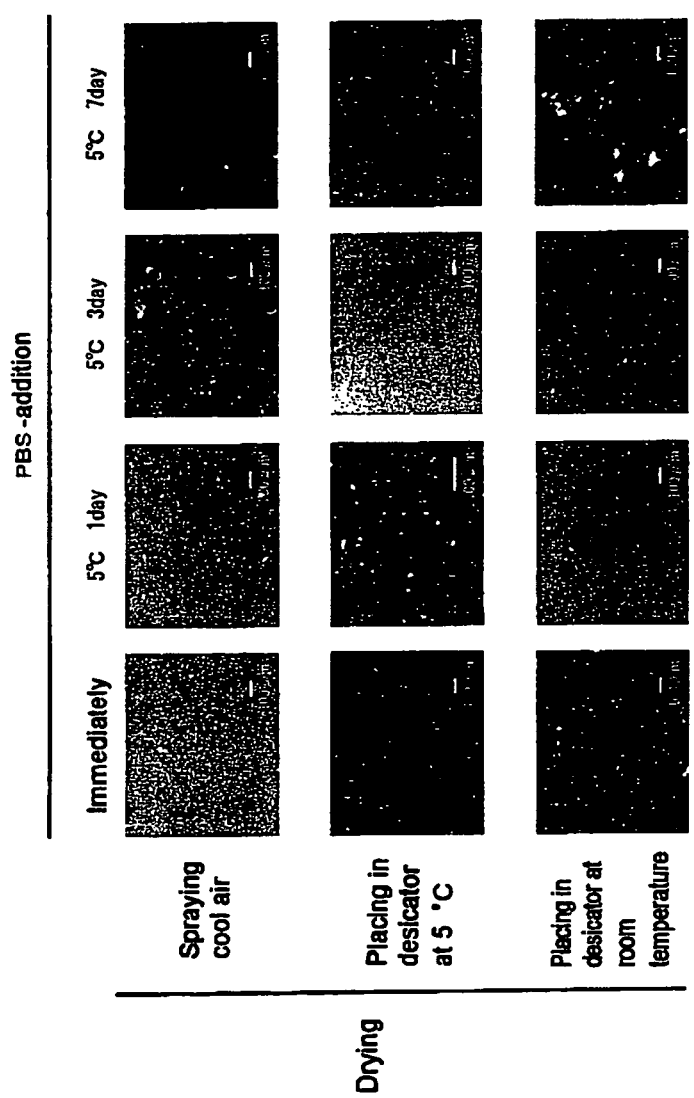
FIG. 19 is a fluorescence micrograph obtained by observing the complexes comprising the plasmid DNA released from the surface of the cell culture instrument according to the present invention with fluorescence microscopy.

Fifty μl of the gel formulation as prepared in Example 10 (10-3, having the composition that was found efficient in transfer efficiency in Example 6) was added dropwise to the bottom of a 96-well microplate, and dried by directly spraying a cool air (room temperature, 2 hours) or by placing in a desicator with silica gel (room temperature, 2 days) so as to prepare a cell culture instrument, of which the cell culture surface is coated with a complex. One hundred μl of 0.01 M phosphate buffer (PBS) that had been adjusted to be isotonic with living bodies by supplementing sodium chloride was added to the wells of the instrument, and the pipetting was slightly conducted immediately for sampling. Further, 100 μl of 0.01 M phosphate buffer (PBS) that had been adjusted to be isotonic with living bodies by supplementing sodium chloride was added to the wells of the instrument, and the instrument was left overnight at 37° C., followed by slightly pipetting for sampling. To 10 μl of the resultant sample, 2 μl of Single-Stranded nucleic acid fluorescence staining regent YOYO (Molecular Probes) was added to stain the oligonucleotides, and the complexes that released form the surface of the instrument were observed by fluorescent microscopy. The fluorescence micrograph is shown in FIG. 19. The complexes having a major axis of 100 μm or less were observed in all of the samples. This means that exposure on PBS allows to release complexes from the surface of a cell culture instrument. The form or the shape of the released complexes was not changed between before and after the coating onto the surface of the instrument irrespective of drying method, and condition of PBS exposure. This shows that the complexes are retained on the surface of a cell culture instrument with keeping their form or shape irrespective of drying method, and that the form or the shape of the complexes maintains in a temperature condition of 37° C. that is usually used in cell culture.

Example 14

Gene Transfer with a Cell Culture Instrument Coated with a Complex

Three hundreds μl of the gel formulations as prepared in Example 10, 10-1, 10-4, and 10-7, comprising pCMV-EGFP were added to a 6-well cell culture microplate, and dried by spraying a cool air so as to prepare a cell culture instrument onto which a complex comprising pCMV-EGFP was coated. As control, 300 μl of an aqueous solution comprising pCMV-EGFP at 100 μg/ml was added to a plate, and dried similarly. Into each well, 7.5×10$^4$ cells of 239 cells were seeded, and a DMEM medium containing 10% FBS was added thereto, followed by culturing at 37° C. From the start of the culture, the medium was replaced with a fresh medium every 4 or 5 days. eleven days after the seeding, the cells were observed by fluorescent microscopy, and the number of the cells expressing GFP was counted to estimate transfer efficiency.

Similarly, 300 μl or 500 μl of the gel formulations as prepared in Example 10, 10-13 to 22, and 24, comprising pCMV-HST-1-IL-2 were added to a 6-well cell culture microplate, and dried by spraying a cool air so as to prepare a cell culture instrument onto which a complex comprising pCMV-HST-1-IL-2 was coated. As control, 300 μl or 500 μl of an aqueous solution comprising pCMV-HST-1-IL-2 at 100 μg/ml, PB solution or PBS solution were added to a plate, and dried similarly.

1) Transfer of Plasmid DNA into 239 Cells

Into each well wherein 300 μl of the gel formulation was coated, 7.5×10$^4$ cells of 239 cells were seeded, and a DMEM medium containing 10% FBS was added thereto, followed by culturing at 37° C. for 10-13 to −19. Eight days after the cell seeding, the medium was replaced, and IL-2 concentration in the medium sampled 11 days later was determined by ELISA (Quamtikine human IL-2 (R&D Systems)). For 10-20 to −22, a DMEM medium was added to the plate, and cultured overnight at 37° C., after which on the following day the medium was replaced with a DMEM medium containing 10% FBS, and then cultured at 37° C. Eight days and 11 days after the cell seeding, the medium was replaced, and IL-2 concentration in the medium sampled 15 days later was determined by ELISA. Further, for 10-20, 21, and 24, a DMEM medium containing 10% FBS was added to the plate, and the plate was cultured at 37° C. IL-2 concentration in the medium sampled 8 days after the cell seeding was determined by ELISA.

2) Transfer of Plasmid DNA into NIH3T3 Cells

Into the well wherein 500 μl of 10-14 to −17 was coated, $5\times10^4$ cells of NIH3T3 cells were seeded, and a DMEM medium containing 10% FBS was added thereto, followed by culturing at 37° C. Eight days after the cell seeding, the medium was sampled, and IL-2 concentration therein was determined by ELISA.

The results as obtained in above 1) and 29 are summarized in Tables 8 and 9. When complexed with a collagen and coated onto a cell culture instrument, both pCMV-EGFP and pCMV-HST-1-IL-2 could be efficiently transferred into 293 cells and NIH3T3 cells. The result shows that the effect of the complexes of the present invention on facilitation of gene transfer is not affected by the kinds of plasmid DNA, species of the cells, and the presence or the absence of serum in the culture. Further, in case of plasmid DNAs, it has been found that coating of the complex having 1112 or less of the nucleotide monomer per one collagen molecule, and having an average major axis of 151 μm or less, provided superior transfer efficiency and gene expression.

TABLE 8

| Sample | Number of nucleotide monomer per collagen molecule | Average major axis of complexes (μm) | transfer efficiency |
| --- | --- | --- | --- |
| Control | | | 0.0028 |
| 10-1 | 2406 | 9.1 | 0.0760 |
| 10-4 | 299 | 53 | 0.0729 |
| 10-7 | 66 | 303 | 0.0374 |

Example 15

Gene Transfer into Cells by Addition of Complexes

Into a 6-well plate, $5\times10^4$ cells of 239 cells were seeded, and cultured in the presence of a DMEM medium containing 10% FBS at 37° C. Three days after the seeding, 300 μl of the gel formulations as prepared in Example 10, 10-1, 10-4, 10-7, 10-8, 10-9, and 10-10, comprising pCMV-EGFP, and a water or a PB solution comprising pCMV-EGFP at 100 μg/ml as control were each added thereto, and the cells were cultured in the presence of a DMEM medium containing 10% FBS at 37° C. On the following day, the media were replaced with a fresh medium, and 13 days later for 10-1, 10-4, and 10-7, or 5 days later for 10-8, 10-9, and 10-10, the cells were observed by fluorescent microscopy, followed by counting the number of the cells expressing GFP.

Similarly, $7.5\times10^4$ cells of 239 cells were seeded into a 6-well plate, and cultured in the presence of a DMEM medium containing 10% FBS at 37° C. Two days after the seeding, 300 μl of the gel formulations as prepared in Example 10, 10-20 and 10-21, comprising pCMV-HST-1-IL-2, and a PB solution comprising pCMV-HST-1-IL-2 at 100 μg/ml as control were each added thereto, and the cells were cultured in the presence of a DMEM medium containing 10% FBS at 37° C. On the following day, the media were replaced with a fresh medium, and 5 days later, the media were sampled, and IL-2 concentration therein were determined by ELISA (Quamtikine human IL-2 (R&D Systems)).

The results are summarized in Tables 10, 11 and 12. When complexed with a collagen and added to cells, both pCMV-EGFP and pCMV-HST-1-IL-2 could be efficiently transferred into the cells. It has been found that in case of the complexes having an average major axis of 53 μm or less as shown in the present Example, the addition of the complex having 2406 or less, and further 701 or less of the nucleotide monomer per one collagen molecule, provided superior transfer efficiency and gene expression.

TABLE 9

| Sample | Cell species | Solvent | Presence or Absence of FBS | Number of nucleotide monomer per collagen molecule | Average major axis of complexes (μm) | IL-2 concentration in media (pg/ml) |
| --- | --- | --- | --- | --- | --- | --- |
| Control | 293 | water | Presence | | | 5.3 |
| 10-13 | 293 | water | Presence | 4228 | 6 | 7.3 |
| 10-14 | 293 | water | Presence | 1122 | 20 | 14.8 |
| 10-15 | 293 | water | Presence | 426 | 6.1 | 19.3 |
| 10-16 | 293 | water | Presence | 324 | 20 | 6.3 |
| 10-17 | 293 | water | Presence | 360 | 16 | 18.2 |
| 10-18 | 293 | water | Presence | 95 | 151 | 8.4 |
| 10-19 | 293 | water | Presence | 66 | 256 | 5.3 |
| Control | 293 | PB | Absence | | | 23.55 |
| 10-20 | 293 | PB | Absence | 701 | 6.1 | 72.93 |
| 10-21 | 293 | PB | Absence | 262 | 20 | 264.61 |
| 10-22 | 293 | PB | Absence | 97 | 25 | 86.22 |
| Control | 293 | PB | Presence | | | 3.35 |
| 10-20 | 293 | PB | Presence | 701 | 6.1 | 21.01 |
| 10-21 | 293 | PB | Presence | 262 | 20 | 86.68 |
| Control | 293 | PBS | Presence | | | 1.07 |
| 10-23 | 293 | PBS | Presence | 315 | 9.8 | 15.26 |
| Control | NIH3T3 | water | Presence | | | 0 |
| 10-14 | NIH3T3 | water | Presence | 1122 | 20 | 0.79 |
| 10-15 | NIH3T3 | water | Presence | 426 | 6.1 | 6.06 |
| 10-16 | NIH3T3 | water | Presence | 324 | 20 | 4.05 |
| 10-17 | NIH3T3 | water | Presence | 360 | 16 | 2.78 |

TABLE 10

| Sample | Solvent | Number of nucleotide monomer per collagen molecule | Average major axis of complexes (μm) | transfer efficiency |
|---|---|---|---|---|
| Control | water | | | 0.0012 |
| 10-1 | water | 2406 | 9.1 | 0.0231 |
| 10-4 | water | 299 | 53 | 0.0247 |
| 10-7 | water | 66 | 303 | 0.0041 |

TABLE 11

| Sample | Solvent | Number of nucleotide monomer per collagen molecule | Average major axis of complexes (μm) | Number of EGFP-expressing cells |
|---|---|---|---|---|
| Control | PB | | | 100 |
| 10-8 | PB | 448 | <3.4 | 128 |
| 10-9 | PB | 152 | 7.7 | 1200 |
| 10-10 | PB | 97 | 22 | 12000 |

TABLE 12

| Sample | Solvent | Number of nucleotide monomer per collagen molecule | Average major axis of complexes (μm) | IL-2 concentration in media (pg/ml) |
|---|---|---|---|---|
| Control | PB | | | 0 |
| 10-20 | PB | 701 | 6.1 | 8.98 |
| 10-21 | PB | 262 | 20 | 76.81 |
| 10-22 | PB | 97 | 25 | 120.74 |

INDUSTRIAL APPLICABILITY

According to the complexes of the present invention, it is possible to preserve and stabilize desired nucleic acids by complexing with collagens or collagen derivatives, 2) to transfer efficiently desired nucleic acids into cells when administered to living bodies, and 3) to express and inhibit desired nucleic acids without reagents for gene transfer. The complexes of the present invention can be applied to various aspects since the complexes of the invention have advantages 1) that DNAs, antisense oligonucleotides and virus vectors can be preserved and stabilized, 2) that the complexes can be stored during a long period of time on plates dried where the complexes are coated, 3) that genes can be expressed without reagents for gene transfer when cells are seeded onto the plates, 4) that kinds of subjects of nucleic acids and methods for immobilization are not limited to specific ones, and 5) that the duration time of the expression in case of plasmid DNAs is excellently extended.

According to the present invention, it is possible to readily examine the functions of genes or proteins, of which the expressions are inhibited by antisense oligonucleotides by determining the proliferation or the morphology of the cells, or the expression levels of cytokines or receptors. Not only antisense oligonucleotides, but also other materials can be complexed with collagens to form complexes, which in turn can be coated onto plates; in case of ribozymes, it is possible to carry out a screening similar to that of antisense oligonucleotides; and further in case of plasmid DNAs or adenoviruses, it is possible to examine the functions of genes or proteins by determining the changes of cells by the expression of certain genes. Collagens or collagen derivatives comprised in the complexes of the present invention have been known to affect no cells, and the screening using the complexes of the present invention makes it possible to carry out the examinations of gene functions that seldom avoid the unspecific affections to cells, which would be induced by conventional reagents for gene transfer.

The invention claimed is:

1. A pharmaceutical preparation for administration to a living body comprising a solution of an electrostatic complex consisting essentially of a double-stranded RNA and a water-soluble atelocollagen, wherein said complex facilitates the transfer of said double-stranded RNA to a target tissue or a target organ and said complex exhibits a major axis of 100 μm or less in length.

2. The preparation according to claim 1, wherein the double-stranded RNA is 5-30 nucleotides in length.

3. The preparation according to claim 1, wherein the double-stranded RNA is an RNA derivative.

4. The preparation according to claim 1, wherein the double-stranded RNA is an RNA comprising a phosphorothioate bond.

5. The preparation according to claim 1, wherein the double-stranded RNA is an RNA comprising an internucleotide comprising a phosphate, sugar or base moiety chemically modified to avoid enzymatic degradations.

6. A pharmaceutical preparation for administration to a living body comprising a solution of an electrostatic complex consisting essentially of an a double-stranded RNA and a water-soluble atelocollagen, wherein said complex facilitates the transfer of said double-stranded RNA to a target tissue or a target organ and said complex exhibits a major axis of 10 μm or less in length.

7. The preparation according to claim 6, wherein the double-stranded RNA is 5-30 nucleotides in length.

8. The preparation according to claim 6, wherein the double-stranded RNA is an RNA derivative.

9. The preparation according to claim 6, wherein the double-stranded RNA is an RNA comprising a phosphorothioate bond.

10. The preparation according to claim 6, wherein the double-stranded RNA is an RNA comprising an internucleotide comprising a phosphate, sugar or base moiety chemically modified to avoid enzymatic degradations.

* * * * *